(12) United States Patent
Martin et al.

(10) Patent No.: US 9,339,441 B2
(45) Date of Patent: *May 17, 2016

(54) ORAL MOUTHPIECE AND METHOD FOR THE USE THEREOF

(71) Applicants: THE UNIVERSITY OF WESTERN ONTARIO, London (CA); TRUDELL MEDICAL INTERNATIONAL, London (CA)

(72) Inventors: Ruth E. Martin, London (CA); Michael Nuttall, London (CA); Bryan Finlay, London (CA); Julie Theurer, London (CA); Brandon Coultes, Ilderton (CA)

(73) Assignees: The University of Western Ontario, London (CA); Trudell Medical International, London (CA)

( * ) Notice: Subject to any disclaimer, the term of this patent is extended or adjusted under 35 U.S.C. 154(b) by 0 days.

This patent is subject to a terminal disclaimer.

(21) Appl. No.: 14/656,385

(22) Filed: Mar. 12, 2015

(65) Prior Publication Data

US 2015/0283035 A1    Oct. 8, 2015

Related U.S. Application Data

(63) Continuation of application No. 13/954,314, filed on Jul. 30, 2013, now Pat. No. 8,992,468, which is a continuation of application No. 13/040,058, filed on Mar. 3, 2011, now Pat. No. 8,517,729.

(Continued)

(51) Int. Cl.
  *A61C 17/00*        (2006.01)
  *A61J 7/00*         (2006.01)
(Continued)

(52) U.S. Cl.
  CPC .............. *A61J 7/0061* (2013.01); *A61H 21/00* (2013.01); *A61H 23/04* (2013.01); *A61M 25/02* (2013.01); *A61M 2025/0206* (2013.01); *A61M 2210/0625* (2013.01)

(58) Field of Classification Search
  CPC .......... A61M 16/0666; A61M 16/049; A61M 2210/0625
  USPC ............... 128/206.29; 433/80, 88; 604/77, 79
  See application file for complete search history.

(56) References Cited

U.S. PATENT DOCUMENTS

| 743,866 A | 11/1903 | Harris |
| 2,672,143 A | 3/1954 | Gold et al. |

(Continued)

FOREIGN PATENT DOCUMENTS

| CA | 2274970 | 10/2006 |
| CA | 2792033 | 9/2011 |

(Continued)

OTHER PUBLICATIONS

Abdelmunim, H. et al., "A 3D Human Database Construction Based on a Point-based Shape Registration," 18th IEEE International Conference on Image Processing, 2011, pp. 1617-1620.

(Continued)

*Primary Examiner* — Gerald Landry, II
(74) *Attorney, Agent, or Firm* — Brinks Gilson & Lione

(57) ABSTRACT

The present invention relates generally to an oral device, or mouthpiece, for delivering a fluid to the mouth or oropharynx of a user. In one embodiment, the oral device includes an intraoral portion, an extraoral portion, and an auxiliary support device that serves to stabilize the oral device. In various embodiments, the auxiliary support device may be configured with ear loops, a support band, a support frame and/or a support member. The intraoral portion generally includes at least one outlet port through which the fluid is delivered to the oral cavity or oropharynx. A method of dispensing a fluid using the oral device is also provided.

12 Claims, 18 Drawing Sheets

Related U.S. Application Data

(60) Provisional application No. 61/310,590, filed on Mar. 4, 2010, provisional application No. 61/311,145, filed on Mar. 5, 2010, provisional application No. 61/417,041, filed on Nov. 24, 2010.

(51) Int. Cl.
*A61H 21/00* (2006.01)
*A61H 23/04* (2006.01)
*A61M 25/02* (2006.01)

(56) References Cited

U.S. PATENT DOCUMENTS

| | | |
|---|---|---|
| 3,118,667 A | 1/1964 | Barons |
| 3,286,576 A | 11/1966 | West |
| 3,646,628 A | 3/1972 | Halford |
| 3,744,485 A | 7/1973 | Worthy |
| 3,867,770 A | 2/1975 | Davis |
| 3,924,850 A | 12/1975 | Robertson |
| 4,170,230 A | 10/1979 | Nelson |
| 4,367,759 A | 1/1983 | Kline |
| 4,401,130 A | 8/1983 | Halford et al. |
| 4,495,944 A | 1/1985 | Brisson et al. |
| 4,519,400 A | 5/1985 | Brenman et al. |
| 4,572,177 A * | 2/1986 | Tiep et al. ............... 128/205.17 |
| 4,608,974 A | 9/1986 | Sicurelli, Jr. |
| 4,718,662 A | 1/1988 | North |
| 4,865,021 A | 9/1989 | Siderman |
| 4,966,580 A | 10/1990 | Turner et al. |
| 4,986,283 A | 1/1991 | Tepper |
| 4,997,182 A | 3/1991 | Kussick |
| 5,066,502 A | 11/1991 | Eales |
| 5,085,634 A | 2/1992 | Lackney |
| 5,133,971 A | 7/1992 | Copelan et al. |
| 5,143,087 A | 9/1992 | Yarkony |
| 5,176,151 A | 1/1993 | Harding |
| 5,191,014 A | 3/1993 | Roberts et al. |
| 5,213,553 A | 5/1993 | Light |
| 5,260,000 A | 11/1993 | Nandu et al. |
| 5,263,976 A | 11/1993 | Williams |
| 5,268,005 A | 12/1993 | Suhonen |
| 5,288,498 A | 2/1994 | Stanley et al. |
| 5,379,648 A | 1/1995 | Tiffin |
| 5,445,825 A | 8/1995 | Copelan et al. |
| H1557 H | 7/1996 | Joubert et al. |
| 5,566,645 A | 10/1996 | Cole |
| 5,735,772 A | 4/1998 | Schiavoni |
| 5,839,444 A | 11/1998 | Komatsu et al. |
| 5,855,908 A | 1/1999 | Stanley et al. |
| 5,897,492 A | 4/1999 | Feller et al. |
| D411,623 S | 6/1999 | Schiavoni |
| 5,954,673 A | 9/1999 | Stachlin et al. |
| 5,993,413 A | 11/1999 | Aaltonen et al. |
| D422,694 S | 4/2000 | Hill |
| D461,558 S | 8/2002 | Schiavoni |
| 6,454,788 B1 | 9/2002 | Ashton |
| 6,468,554 B1 | 10/2002 | Ichino |
| 6,581,605 B2 | 6/2003 | Addington et al. |
| 6,591,140 B2 | 7/2003 | Strome et al. |
| 6,607,549 B2 | 8/2003 | Huang |
| 6,632,095 B2 | 10/2003 | Ryan |
| 6,823,554 B1 | 11/2004 | Braun et al. |
| 6,974,424 B2 | 12/2005 | Fletcher et al. |
| 7,083,548 B1 | 8/2006 | Moore et al. |
| 7,143,462 B2 | 12/2006 | Hohlbein |
| 7,238,144 B2 | 7/2007 | Ferrara |
| 7,238,145 B2 | 7/2007 | Robbins et al. |
| 7,258,311 B2 | 8/2007 | Yen et al. |
| 7,273,327 B2 | 9/2007 | Hohlbein et al. |
| 7,404,403 B2 | 7/2008 | Farrell |
| 7,438,667 B2 | 10/2008 | Robbins et al. |
| 7,527,642 B2 | 5/2009 | VanSkiver et al. |
| 7,606,623 B2 | 10/2009 | Ludlow et al. |
| 7,660,636 B2 | 2/2010 | Castel et al. |
| 7,662,066 B2 | 2/2010 | Ferrara |
| 7,942,782 B2 | 5/2011 | Al-Tawil |
| 8,047,964 B2 | 11/2011 | Al-Tawil |
| 8,517,729 B2 | 8/2013 | Martin et al. |
| 2004/0000054 A1 | 1/2004 | Sommer |
| 2005/0103331 A1 | 5/2005 | Wedemeyer |
| 2006/0042638 A1 | 3/2006 | Niklewski et al. |
| 2006/0210480 A1 | 9/2006 | Hamdy |
| 2006/0235352 A1 | 10/2006 | Dziewas et al. |
| 2006/0278232 A1 | 12/2006 | Nichols |
| 2006/0282010 A1 | 12/2006 | Martin et al. |
| 2007/0000495 A1 | 1/2007 | Matula, Jr. et al. |
| 2007/0181144 A1 | 8/2007 | Brown et al. |
| 2007/0272247 A1 | 11/2007 | Porat |
| 2008/0190436 A1 * | 8/2008 | Jaffe et al. ............... 128/207.18 |
| 2009/0123886 A1 * | 5/2009 | Vaska ............... 433/27 |
| 2009/0133699 A1 | 5/2009 | Nalagatla et al. |
| 2009/0188520 A1 | 7/2009 | Brown |
| 2009/0249571 A1 | 10/2009 | Rohrig |
| 2009/0259310 A1 | 10/2009 | Blom |
| 2009/0286237 A1 | 11/2009 | Fitzgerald et al. |
| 2009/0306626 A1 | 12/2009 | Sinha et al. |
| 2009/0306741 A1 | 12/2009 | Hogle et al. |
| 2010/0010400 A1 | 1/2010 | Martin et al. |
| 2010/0016908 A1 * | 1/2010 | Martin ............... A61M 11/00 607/3 |
| 2010/0055233 A1 | 3/2010 | Macinnis et al. |
| 2010/0119992 A1 | 5/2010 | Satoh et al. |
| 2010/0121224 A1 | 5/2010 | Toyota et al. |
| 2010/0139664 A1 | 6/2010 | Curti et al. |
| 2010/0311007 A1 * | 12/2010 | Eliyahov ............... A61H 13/00 433/80 |
| 2011/0130249 A1 | 6/2011 | Mikhailenok et al. |
| 2011/0282248 A1 | 11/2011 | Martin et al. |
| 2011/0315141 A1 * | 12/2011 | Lavi ............... A61M 16/0488 128/204.23 |

FOREIGN PATENT DOCUMENTS

| | | |
|---|---|---|
| CN | 201393517 Y | 2/2010 |
| EP | 1055491 B1 | 1/2003 |
| GB | 2159720 B | 12/1985 |
| GB | 2323026 B | 9/1998 |
| JP | 2005-287712 A | 10/2005 |
| JP | 2006-034916 A | 2/2006 |
| JP | 2007-319303 A | 12/2007 |
| JP | 2008-110024 A | 5/2008 |
| WO | WO 01/62325 A1 | 8/2001 |
| WO | WO 2006/036597 A1 | 4/2006 |
| WO | WO 2006/116843 A1 | 11/2006 |
| WO | WO 2007/121065 A2 | 10/2007 |
| WO | WO 2008/048911 A2 | 4/2008 |
| WO | WO 2009/127947 A2 | 10/2009 |
| WO | WO 2012/090507 A1 | 7/2012 |

OTHER PUBLICATIONS

Ada, Louise et al., "Effect of muscle length on strength and dexterity after stroke," Clinical Rehabilitation, vol. 14, 2000, pp. 55-61.

Adams, M.J. et al., "Friction and lubrication of human skin," Tribology Letters, vol. 26, No. 3, Jun. 2007, pp. 239-253.

Addington, Robert W. et al., "Assessing the Laryngeal Cough Reflex and the Risk and the Risk of Developing Pneumonia After Stroke: An Interhospital Comparison," Stroke, vol. 20, 1999, pp. 1203-1207.

Anderson, D.J., "Measurement of Stress in Mastication. I," Journal of Dental Research, vol. 35, 1956, pp. 664-670.

Anderson, D.J., "Measurement of Stress in Mastication. II," Journal of Dental Research, vol. 35, 1956, pp. 671-673.

Baijens, Laura W. et al., "Effects of Therapy for Dysphagia in Parkinson's Disease: Systematic Review," Dysphagia, vol. 24, 2009, pp. 91-102.

Baijens, Laura W. et al., "Rehabilitation Program for Prosthetic Tracheojejunal Voice Production and Swallowing Function Following Circumferential Pharyngolaryngectomy and Neopharyngeal Reconstruction with a Jejunal Free Flap," Dysphagia, vol. 26(1), 2011, published online Apr. 3, 2010, pp. 78-84.

(56) References Cited

OTHER PUBLICATIONS

Barritt, Andrew W. et al., "Role of Cerebral Cortex Plasticity in the Recovery of Swallowing Function Following Dysphagic Stroke," Dysphagia, vol. 24, 2009, pp. 83-90.
Barry, M. et al., "Design of dynamic test equipment for the testing of dental implants," Materials and Design, vol. 26, 2005, pp. 209-216.
Bateman, Claire et al., "Adult Dysphagia Assessment in the UK and Ireland: Are SLTs Assessing the Same Factors?," Dysphagia, vol. 22, 2007, pp. 174-186.
Baylow, Hope E. et al., "Accuracy of Clinical Judgment of the Chin-Down Posture for Dysphagia During the Clinical/Bedside Assessment as Corroborated by Videofluroscopy in Adults with Acute Stroke," Dysphagia, vol. 24, 2009, pp. 423-433.
Becker, Regine et al., "Functional Dysphagia Therapy and PEG Treatment in an Clinical Geriatric Setting," Dysphagia, vol. 26(2), 2011, published online Jan. 26, 2010, pp. 108-116.
Bekelis, Kimon et al., "Severe Dysphagia Secondary to Posterior C1-C3 Instrumentation in a Patient with Altantoaxial Traumatic Injury: A Case Report and Review of the Literature," Dysphagia, vol. 25(2), 2010, published online Sep. 30, 2009, pp. 156-160.
Bennett, Janice W. et al., "Sip-Sizing Behaviors in Natural Drinking Conditions Compared to Instructed Experimental Conditions," Dysphagia, vol. 24, 2009, pp. 152-158.
Bhatka, R. et al., "Bolus size unilateral chewing cycle kinematics," Archrives of Oral Biology, vol. 49, 2004, pp. 559-566.
Billard, Aude et al., "Learning human arm movements by imitation: Evaluation of a biologically inspired connectionist architecture," Robotics and Autonomous Systems, vol. 37, 2001, pp. 145-160.
Bogaardt, H. C. et al., "Cross-cultural Adaptation and Validation of the Dutch Version of SWAL-QoL," Dysphagia, vol. 24, 2009, pp. 66-70.
Bollschweiler, Elfriede et al., "Prevalence of Dysphagia in Patients with Gastroesophageal Reflux in Germany," Dysphagia, vol. 23, 2008, pp. 172-176.
Boryor, Andrew et al., "A downloadable meshed human canine tooth model with PDL and bone for finite element simulations," Dental Materials, vol. 25, 2009, pp. e57-e62.
Bourne, Malcolm, "Relation Between Texture and Mastication," Journal of Texture Studies, vol. 35, 2004, pp. 125-143.
Bülow, Margareta et al., "Neuromuscular Electrical Stimulation (NMES) in Stroke Patients with Oral and Pharyngeal Dysfunction," Dysphagia, vol. 23, 2008, pp. 302-309.
Burkhead, Lori M. et al., "Strength-Training Exercise in Dysphagia Rehabilitation: Principles, Procedures, and Directions for Future Research," Dysphagia, vol. 22, 2007, pp. 251-265.
Butler, Susan G. et al., "Preliminary Investigation of Swallowing Apnea Duration and Swallow/Respiratory Phase Relationships in Individuals with Cerebral Vascular Accident," Dysphagia, vol. 22, 2007, pp. 215-224.
Canning, Brendan J., "Encoding of the cough reflex," Pulmonary Pharmacology & Therapeutics, vol. 20, 2007, pp. 396-401.
Canning, Colleen G. et al., "Loss of strength contributes more to physical disability after stroke than loss of dexterity," Clinical Rehabilitation, vol. 18, 2004, pp. 300-308.
Carlson, Matthew L. et al., "Surgical Management of Dysphagia and Airway Obstruction in Patients with Prominent Ventral Cervical Osteophytes," Dysphagia, vol. 26(1), 2011, published online Jan. 23, 2010, pp. 34-40.
Cha, Tae-Hyun et al., "Noninvasive Treatment Strategy for Swallowing Problems Related to Prolonged Nonoral Feeding in Spinal Muscular Atrophy Type II," Dysphagia, vol. 25(3), 2010, published online Jan. 20, 2010, pp. 261-264.
Chang, Chia-Chi et al., "Effects of a feeding skills training programme on nursing assistants and dementia patients," Care of Older People, © 2005, Blackwell Publishing Ltd., pp. 1185-1192.
Chen, Po-Hung et al., "Prevalence of Perceived Dysphagia and Quality-of-Life Impairment in a Geriatric Population," Dysphagia, vol. 24, 2009, pp. 1-6.

Chin, Ronald Y. et al., "Dysphagia After Emergency Intubation: Case Report and Literature Review," Dysphagia, vol. 24, 2009, pp. 105-108.
Clayton, Nicola A. et al., "Management of Dysphagia in Toxic Epidermal Necrolysis (TEN) and Stevens-Johnson Syndrome (SJS)," Dysphagia, vol. 22, 2007, pp. 187-192.
Colodny, Nancy EdD, "Validation of the Caregiver Mealtime and Dysphagia Questionnaire (CMDQ)," Dysphagia, vol. 23, 2008, pp. 47-58.
Coulas, Véronique et al., "Differentiating Effortful and Noneffortful Swallowing with a Neck Force Transducer: Implications for the Development of a Clinical Feedback System," Dysphagia, vol. 24, 2009, pp. 7-12.
Crary, Michael A. PhD et al., "Identification of Swallowing Events from sEMG Signals Obtained from Healthy Adults," Dysphagia, vol. 22, 2007, pp. 94-99.
Crary, Michael A. PhD et al., "Electrical Stimulation Therapy for Dysphagia: Descriptive Results of Two Surveys," Dysphagia, vol. 22, 2007, pp. 165-173.
Crawford, Hannah et al., "Compliance with Dysphagia Recommendations by Carers of Adults with Intellectual Impairment," Dysphagia, vol. 22, 2007, pp. 326-334.
Danneskiold-Samsøe, B. et al., "Isokinetic and isometric muscle strength in a healthy population with special reference to age and gender," Acta Physiol., vol. 197 (Suppl. 673), 2009, pp. 1-68.
Dantas, Roberto Oliveira et al., "Effect of Gender on Swallow Event Duration Assessed by Videofluroscopy," Dysphagia, vol. 24, 2009, pp. 280-284.
Di Domizio, Jennifer et al., "Forearm posture and grip effects during push and pull tasks," Ergonomics, vol. 53, No. 3, Mar. 2010, pp. 336-343.
Dörfer, Christof E. et al., "Factors influencing proximal dental contact strengths," Eur. J. Oral Sci., vol. 108, 2000, pp. 368-377.
Duizer, L.M. et al., "Instrumental Measures of Bite Forces Associated with Crisp Products," Journal of Texture Studies, vol. 37, 2006, pp. 1-15.
Dyer, Jill C. et al., "Objective Computer-Based Assessment of Valleculae Residue—Is It Useful,?" Dysphagia, vol. 23, 2008, pp. 7-15.
Dziewas, R. et al., "Placing nasogastric tubes in stroke patients with dysphagia: efficiency and tolerability of the reflex placement," J. Neutral Neurosurg. Psychiatry, vol. 74, 2003, pp. 1429-1431.
Easterling, Caryn, "Does an Exercise Aimed at Improving Swallow Function Have an Effect on Vocal Function in the Healthy Elderly?," Dysphagia, vol. 23, 2008, pp. 317-326.
Easterling, Caryn S. et al., "Dementia and Dysphagia," Geriatric Nursing, vol. 29, No. 4, 2008, pp. 275-285.
Eisenberg, John M. MD et al., "8: Diagnosis and Treatment of Swallowing Disorders (Dysphagia) in Acute-Care Stroke Patients," AHRQ Evidence Reports, Agency for Health Care Policy and Research, U.S. Department of Health and Human Services, ECRI, Plymouth Meeting, Pennsylvania, Jul. 1999, 153 pages.
Emami, Mohammad Hassan et al., "Pneumatic Balloon Dilation Therapy Is as Effective as Esophagomyotomy for Achalasia," Dysphagia, vol. 23, 2008, pp. 155-160.
Engelen, L. et al., "Relating Particles and Texture Perception," Chapter 5, pp. 58-72.
Farahmand, Bahram et al., "Predicting fracture and fatigue crack growth properties using tensile properties," Engineering Fracture Mechanics, vol. 75, 2008, pp. 2144-2155.
Ferrario, Virgilio F. et al., "Maximal bite forces in healthy young adults as predicted by surface electromyography," Journal of Dentistry, vol. 32, 2004, pp. 451-457.
Ferrario, V.F. et al., "Single tooth bite forces in healthy young adults," Journal of Oral Rehabilitation, vol. 31, 2004, pp. 18-22.
Finney, M. et al., "Measurement of Biting Velocities at Predetermined and Individual Crosshead Speed Instrumental Imitative Tests for Predicting Sensory Hardness of Gelatin Gels," Journal of Sensory Studies, vol. 20, 2005, pp. 114-129.
Font, Jean Paul MD et al., "Esophargeal Dysphagia," University of Texas Medical Branch, Department of Otolaryngology, Grand Rounds Presentation, Feb. 6, 2008, 53 pages.

(56) References Cited

OTHER PUBLICATIONS

Foster, K.D. et al., "Effect of Texture of Plastic and Elastic Model Foods on the Parameters of Mastication," J. Neurophysiol, vol. 95, 2006, pp. 3469-3479.
Franssen, Oliver et al., "New high modulus silicone elastomer—fiber-reinforced LSR," Rubber World, Jun. 2011, 4 pages.
Frazier, Jacqueline Bolders, "Effect of Tactile Stimulation on Lingual Motor Function in Pediatric Lingual Dysphagia," Dysphagia, vol. 22, 2007, pp. 340-342.
French, Stephen et al., "Recent advances in the physiology of eating," Proceedings of the Nutrition Society, vol. 61, Issue 04, Nov. 2002, pp. 489-496.
Fucile, Sandra et al., "A Contolled-flow Vacuum-free Bottle System Enhances Preterm Infants' Nutritive Sucking Skills," Dysphagia, vol. 24, 2009, pp. 145-151.
Gallagher, Louise et al., "Prescription Drugs and Their Effects on Swallowing," Dysphagia, vol. 24, 2009, 159-166.
Gallas, Syrine et al., "Sensory Transcutaneous Electrical Stimulation Improves Post-Stroke Dysphagic Patients," Dysphagia, vol. 25(4), 2010, published online Oct. 24, 2009, pp. 291-297.
Garcia, Jane Mertz PhD et al., "Serving Temperature Viscosity Measurements of Nectar- and Honey-Thick Liquids," Dysphagia, vol. 23, 2008, pp. 65-75.
Geddes, Donna T. et al., "Ultrasound Imaging of Infant Swallowing During Breast-Feeding," Dysphagia, vol. 25(3), 2010, published online Jul. 22, 2009, pp. 183-191.
Gielo-Perczak, Krystyna, "Mechanical considerations for biomechanical glenohumeral joint modeling," Occupational Ergonomics, vol. 5, 2005, pp. 29-42.
Gomes, Fernanda Rodrigues et al., "Oral and Pharyngeal Transit of a Paste Bolus in Chagas' Disease," Dysphagia, vol. 23, 2008, pp. 82-87.
Gumbley, Freya et al., "Effects of Bolus Volume on Pharyngeal Contact Pressure During Normal Swallowing," Dysphagia, vol. 23, 2008, pp. 280-285.
Hammond, Carol A. Smith et al., "Cough and Aspiration of Food and Liquids Due to Oral-Pharyngeal Dysphagia," Chest, vol. 129,1, Jan. 2006, pp. 154S-168S.
Hammond, Carol Smith, "Cough and Aspiration of Food and Liquids Due to Oral Pharyngeal Dysphagia," Lung, vol. 186 (Suppl 1), 2008, pp. S35-S40.
Han, Tai Ryoon et al., "The Prediction of Persistent Dysphagia Beyond Six Months After Stroke," Dysphagia, vol. 23, 2008, pp. 59-64.
Han, Tai Ryoon et al., "Dysphagia Development after Surgery Unrelated to Laryngeal and Pharyngeal Structures," Dysphagia, vol. 24, 2009, pp. 167-171.
Hanna, Fady et al, "Anthropometric and Demographic Correlates of Dual-Axis Swallowing Accelerometry Signal Characteristics: A Canonical Correlation Analysis," Dysphagia, vol. 25(2), 2010, published online Jun. 3, 2009, pp. 94-103.
Hegland, Karen W. et al., "Volitional control of reflex cough," J. Appl. Physiol., vol. 113, 2012, First published Apr. 5, 2012, pp. 39-46.
Hewitt, Angela MS et al., "Standardized Instrument for Lingual Pressure Measurement," Dysphagia, vol. 23, 2008, pp. 16-25.
Humbert, Ianessa A. PhD et al., "Normal Swallowing and Functional Magnetic Resonance Imaging: A Systematic Review," Dysphagia, vol. 22, 2007, pp. 266-275.
Igarashi, Atsuko et al., "Sensory and Motor Responses of Normal Young Adults During Swallowing of Foods with Different Properties and Volumes," Dysphagia, vol. 25(3), 2010, published online Aug. 13, 2009, pp. 198-206.
Imoto, Yoshimasa et al., "Cough reflex induced by capsaicin inhalation in patients with dysphagia," Acta Oto-Laryngologica, vol. 131, 2011, pp. 96-100.
Inamoto, Yoko et al., "Evaluation of Swallowing Using 320-detector-row Multislice CT. Part II: Kinematic Analysis of Laryngeal Closure during Normal Swallowing," Dysphagia, vol. 26(3), 2011, published online Mar. 5, 2010, pp. 209-217.
Ioakimidis, Ioannis et al., "Food intake and chewing in women," Neurocomputing, vol. 84, 2012, pp. 31-38.
Isaksson, Ulf et al., "Physically violent behavior in dementia care: Characteristics of residents and management of violent situations," Aging & Mental Health, vol. 15, No. 5, Jul. 2011, pp. 573-579.
Isildak, Huseyin et al., "Unusual Manifestations of Bilateral Carotid Artery Dissection: Dysphagia and Hoarseness," Dysphagia, vol. 25(4), 2010, pp. 338-340.
Jaric, Slobodan, "Muscle Strength Testing—Use for Normalisation for Body Size," Sports Med., vol. 32(10), 2002, pp. 615-631.
Jones, B. et al., "ACR Appropriateness Criteria® dysphagia," American College of Radiology, Mar. 2001, 9 pages.
Jones, Harrison N. et al., "Oropharyngeal Dysphagia in Infants and Children with Infantile Pompe Disease," Dysphagia, vol. 25(4), 2010, published online Sep. 10, 2009, pp. 277-283.
Kagaya, Hitoshi et al., "Simple Swallowing Provocation Test Has Limited Applicability as a Screening Tool for Detecting Aspiration, Silent Aspiration, or Penetration," Dysphagia, vol. 25, 2010, pp. 6-10.
Kantor, MacKinlay, "Behold the Brown-Faced Men," The Saturday Evening Post, Sep. 23, 1939, pp. 26, 30, 44, 46, 47, 50, 51 and 54.
Kamegai, Tetsuya et al., "A determination of bit force in northern Japanese children," Eur. J. of Orthodontics, vol. 27, 2005, pp. 53-57.
Kanai, Naoko et al., "Successful Treatment of Pulmonary Aspiration Due to Brain Stem Infarction by Using Cough Exercise Based on Swallowing Scintigraphy: Preliminary Observations," Dysphagia, vol. 24, 2009, pp. 434-437.
Karaman, Emin et al., "Unusual Location of Primary Hydatid Cyst: Soft Tissue Mass in the Parapharyngeal Region," Dysphagia, vol. 26(1), 2011, published online Mar. 4, 2010, pp. 75-77.
Katsinelos, Panagiotis, MD, PhD. et al., "Congenital Bilateral Pharyngoceles: An Unusual Case of Upper Dysphagia," Dysphagia, vol. 23, 2008, pp. 98-100.
Katsinelos, Panagiotis et al., "Long-term Botulinum Toxin Treatment for Dysphagia Due to Large Epiphrenic Diverticulum in Elderly Patients: A Report of Two Cases," Dysphagia, vol. 24, 2009, pp. 109-113.
Kellen, Patrick M. et al., "Computer-Assisted Assessment of Hyoid Bone Motion from Videofluoroscopic Swallow Studies," Dysphagia, vol. 25(4), 2010, published online Oct. 24, 2009, pp. 298-306.
Kelly, Jennifer et al., "A Qualitative Study of the Problems Surrounding Medicine Administration to Patients with Dysphagia," Dysphagia, vol. 24, 2009, pp. 49-56.
Kennedy, Daniel et al., "Tongue Pressure Patterns During Water Swallowing," Dysphagia, vol. 25, 2010, pp. 11-19.
Kieser, Jules et al., "Measuring Intraoral Pressure: Adaptation of a Dental Appliance Allows Measurement During Function," Dysphagia, vol. 23, 2008, pp. 237-243.
Kim, Youngsun PhD et al., "Stage Transition Duration in Patients Poststroke," Dysphagia, vol. 22, 2007, pp. 299-305.
Kim, Youngsun et al., "Maximal Hyoid Displacement in Normal Swallowing," Dysphagia, vol. 23, 2008, pp. 274-279.
Kim, Youngsun et al., "Maximal Hyoid Excursion in Poststroke Patients," Dysphagia, vol. 25, 2010, pp. 20-25.
Kind, Amy et al., "Omission of Dysphagia Therapies in Hospital Discharge Communications," Dysphagia, vol. 26(1), 2011, published online Jan. 23, 2010, pp. 49-61.
Klatsky, Meyer D.D.S., "Cinephotography and Cinefluorography of the Masticatory Apparatus in Function," American Journal of Orthodontics and Oral Surgery, vol. 25, No. 3, Mar. 1939, pp. 205-210.
Kluin, Karen J. et al., "Dysphagia in elderly men with myasthenia gravis," Journal of the Neurological Sciences, vol. 138, 1996, pp. 49-52.
Koc, Duygu et al., "Bite Force and Influential Factors on Bite Force Measurements: A Literature Review," European Journal of Dentistry, vol. 4, Apr. 2010, pp. 223-232.
Koolstra, J.H. et al., "Dynamics of the Human Masticatory Muscles During a Jaw Open-Close Movement," J. Biomechanics, vol. 30, No. 9, 1997, pp. 883-889.
Koolstra, J.H., "Dynamics of the Human Masticatory System," Crit. Rev. Oral Biol. Med., vol. 13(4), 2002, pp. 366-376.

(56) References Cited

OTHER PUBLICATIONS

Kos, Martijn P. et al., "Long-Term Results of External Upper Esophageal Sphincter Myotomy for Oropharyngeal Dysphagia," Dysphagia, vol. 25(3), 2010, published online Sep. 17, 2009, pp. 169-176.
Krause, Eike et al., "Botulinum Toxin A Treatment of Cricopharyngeal Dysphagia After Subarachnoid Hemorrhage," Dysphagia, vol. 23, 2008, pp. 406-410.
Kvist, L. Catharina et al., "Equipment for drug release testing of medicated chewing gums," Journal of Pharmaceutical and Biomedical Analysis, vol. 22, 2000, pp. 405-411.
Lamm, Nyla Claire, et al., A Comment on "Effect of Tactile Stimulation on Lingual Motor Function in Pediatric Lingual Dysphagia," Dysphagia, vol. 22, 2007, pp. 343-352.
Landreneau, Stephen W. et al., "Dysphagia in a patient with Esophageal Intramural Pseudo-diverticulosis," Visible Human Journal of Endoscopy, vol. 10, Issue 1, 2011, 3 pages.
Lang, Ivan M., "Brain Stem Control of the Phases of Swallowing," Dysphagia, vol. 24, 2009, pp. 333-348.
Laubach, Lloyd L., "Chapter VII—Human Muscular Strength," Anthropology Research Project Web Associates, pp. VII-1-VII-55.
Lazenby, Tracy, "The Impact of Aging on Eating, Drinking, and Swallowing Function in People with Down's Syndrome," Dysphagia, vol. 23, 2008, pp. 88-97.
Leach, Chet PhD et al., "Particle size of inhaled corticosteroids: Does it matter?" J. Allergy Clin. Immunol., vol. 124, No. 6, pp. S88-S93.
Leder, Steven B. et al., "Confirmation of No Causal Relationship Between Tracheotomy and Aspiration Status: A Direct Replication Study," Dysphagia, vol. 25, 2010, pp. 35-39.
Lee, Joon et al., "Effects of Age and Stimulus on Submental Mechanomyography Signals During Swallowing," Dysphagia, vol. 24, 2009, pp. 265-273.
Lee, Shin-Jae et al., "Cluster analysis of tooth size in subjects with normal occlusion," American Journal of Orthodontics and Dentofacial Orthopedics, vol. 132, No. 6, Dec. 2007, pp. 796-800.
Leonard, Rebecca et al., "Fluoroscopic Surrogate for Pharyngeal Strength: The Pharyngeal Constriction Ratio (PCR)," Dysphagia, vol. 26(1), 2011, published online Oct. 24, 2009, pp. 13-17.
Leopold, Norman A. et al., "Supranuclear Control of Swallowing," Dysphagia, vol. 25(3), 2010, published online Sep. 3, 2009, pp. 250-257.
Leow, Li Pyn et al., "The Impact of Dysphagia on Quality of Life in Ageing and Parkinson's Disease as Measured by the Swallowing Quality of Life (SWAL-QOL) Questionnaire," Dysphagia, vol. 25(3), 2010, published online Aug. 13, 2009, pp. 216-220.
Leslie, Paula, PhD et al., "Cervical Auscultation Synchronized with Images from Endoscopy Swallow Evaluations," Dysphagia, vol. 22, 2007, pp. 290-298.
Leslie, Paula et al., "People with a Learning Disability and Dysphagia: A Cinderella Population," Dysphagia, vol. 24, 2009, pp. 103-104.
Lever, Teresa E. et al., "The Effect of an Effortful Swallow on the Normal Adult," Dysphagia, vol. 22, 2007, pp. 312-325.
Lever, Teresa E. et al., "A Mouse Model of Pharyngeal Dysphagia in Amyotrophic Lateral Sclerosis," Dysphagia, Springer Science & Business Media, Jun. 3, 2009, 15 pages.
Lever, Teresa E. et al., "An Animal Model of Oral Dysphagia in Amyotrophic Lateral Sclerosis," Dysphagia, vol. 24, 2009, pp. 180-195.
Lewis, Jr. James L., "Operator Performance and Localized Muscle Fatigue in a Simulated Space Vehicle Control Task," NASA Technical Memorandum 58220, Jun. 1979, 83 pages.
Lim, Anthony et al., "A Pilot Study of Respiration and Swallowing Integration in Parkinson's Disease: "On" and "Off" Levodopa," Dysphagia, vol. 23, 2008, pp. 76-81.
Logemann, Jeria A. et al., "What Information Do Clinicians Use in Recommending Oral versus Nonoral Feeding in Oropharyngeal Dysphagic Patients,?" Dysphagia, vol. 23, 2008, pp. 378-384.
Logemann, Jeri A., "A Randomized Study Comparing the Shaker Exercise with Traditional Therapy: A Preliminary Study," Dysphagia, vol. 24, 2009, pp. 403-411.
Lundgren, D. et al., "Occlusal force pattern during chewing and biting in dentitions restored with fixed bridges of cross-arch extension," Journal of Oral Rehabilitation, vol. 13, 1986, pp. 57-71.
Lunt, Darin R. et al., "Impact energy absorption of three mouthguard materials in three environments," Dental Traumatology, vol. 26, 2010, pp. 23-29.
Maclean, Julia et al., "Post-Laryngectomy: It's Hard to Swallow," Dysphagia, vol. 24, 2009, pp. 172-179.
Maclean, Julia et al., "Dysphagia Following a Total Laryngectomy: The Effect on Quality of Life, Functioning, and Psychological Well-Being," Dysphagia, vol. 24, 2009, pp. 314-321.
Maeshima, Shinichiro, MD, PhD et al., "Influence of Dysphagia on Short-Term Outcome in Patients with Acute Stroke," Am. J. Phys. Med. Rehabil., vol. 90, No. 4, Apr. 2011, pp. 316-320.
Malandraki, Georgia A. et al., "Age-Related Differences in Laterality of Cortical Activations in Swallowing," Dysphagia, vol. 25(3), 2010, published online Sep. 17, 2009, pp. 238-249.
Marbach, Joseph J. D.D.S., "Phantom bite," Am. J. Orthod., vol. 70, No. 2, Aug. 1976, pp. 190-199.
Martin, Ruth E., "Neuroplasticity and Swallowing," Dysphagia, vol. 24, 2009, pp. 218-229.
Martin-Harris, Bonnie et al., "MBS Measurement Tool for Swallow Impairment—MBSImp: Establishing a Standard," Dysphagia, vol. 23, 2008, pp. 392-405.
Martin-Harris, Bonnie et al., "Erratum to: MBS Measurement Tool for Swallow Impairment—MBSImp: Establishing a Standard," Dysphagia, vol. 25, 2010, p. 79.
Martino, Rosemary et al., "Perceptions of Psychological Issues Related to Dysphagia Differ in Acute and Chronic Patients," Dysphagia, vol. 25, 2010, pp. 26-34.
Márton, Krisztina et al., "Evaluation of oral manifestations and masticatory force in patients with polymyositis and dermatomyositis," J. Oral Pathol. Med., vol. 34, 2005, pp. 164-169.
Materazzi, S. et al., "Cough Sensors. II. Transient Receptor Potential Membrane Receptors on Cough Sensors," Handbook Exp. Pharmacol., vol. 187, 2009, pp. 49-61.
Mazari, A. et al., "Contribution of the Cheeks to the Intraoral Manipulation of Food," Dysphagia, vol. 22, 2007, pp. 117-121.
McElhiney, Judith et al., "The Mayo Dysphagia Questionnaire-30: Documentation of Reliability and Validity of a Tool for Interventional Trials in Adults with Esophageal Disease," Dysphagia, vol. 25(3), 2010, published online Oct. 24, 2009, pp. 221-230.
McHorney, Colleen A., "Clinical Validity of the SWAL-QOL and SWAL-CARE Outcome Tools with Respect to Bolus Flow Measures," Dysphagia, vol. 23, 2008, p. 461.
McKinstry, Anita et al., "Outcomes of Dysphagia Intervention in a Pulmonary Rehabilitation Program," Dysphagia, vol. 25(2), 2010, published online Jul. 18, 2009, pp. 104-111.
Meng, Han et al., "Anatomical Variations in Stylopharyngeus Muscle Insertions Suggest Interindividual and Left/Right Differences in Pharyngeal Clearance Function of Elderly Patients: A Cadaveric Study," Dysphagia, vol. 23, 2008, pp. 251-257.
Mepani, Rachel et al., "Augmentation of Deglutitive Thyrohyoid Muscle Shortening by the Shaker Exercise," Dysphagia, vol. 24, 2009, pp. 26-31.
Metheny, Norma A., "Preventing Aspiration in Older Adults with Dysphagia," Medsurg Nursing, vol. 15, 2, ProQuest Nursing & Allied Health Source, Apr. 2006, pp. 110.
Miller, Jeri L. et al., "Preliminary Ultrasound Observation of Lingual Movement Patterns During Nutritive versus Non-nutritive Sucking in a Premature Infant," Dysphagia, vol. 22, 2007, pp. 150-160.
Minami, Ichiro et al., "Jaw-movement smoothness during empty chewing and gum chewing," European Journal of Oral Sciences, vol. 120, 2012, pp. 195-200.
Miura, H. et al., "Relationship between cognitive function and mastication in elderly females," Journal of Oral Rehabilitation, vol. 30, 2003, pp. 808-811.
Miyaura, K. et al., "Comparison of biting forces in different age and sex groups: a study of biting efficiency with mobile and non-mobile teeth," Journal of Oral Rehabilitation, vol. 26, 1999, pp. 223-227.

(56) References Cited

OTHER PUBLICATIONS

Moore, Jill, "Dysphagia Screening," Integris Stroke Center of Oklahoma, Southwest Medical Center, Acute Physical Medicine Department, Slide presentation, date unknown, 20 pages.
Monroe, Kimberly, "Revisiting the basics of successful ergonomics programs," Ergonomics 101, Industrial Engineer, vol. 38, 3, Mar. 2006, pp. 41-45.
Morinière, Sylvain et al., "Origin of the Sound Components During Pharyngeal Swallowing in Normal Subjects," Dysphagia, vol. 23, 2008, pp. 267-273.
Murray, Joseph, PhD, "Accuracy of Dysphagia Assessment," VA Ann Arbor, Wayne State University, Detroit, date unknown, 96 pages.
Nagaoka, Keiko, PhD. et al., "Activities of the Muscles Involved in Swallowing in Patients with Cleft Lip and Palate," Dysphagia, vol. 22, 2007, pp. 140-144.
Nakajima, Makoto et al., "Clinical Significance of Oral Intake in Patients with Acute Stroke," Dysphagia, vol. 25(3), 2010, published online Aug. 5, 2009, pp. 192-197.
Neumann, H.H., "Electrical Action Currents During Mastication: Measurement of the Effort Exerted in Chewing Various Foods," Journal of Dental Research, Aug. 1950, Downloaded Mar. 10, 2011, Sage Publications, 7 pages.
Nguyen, C.T. et al., "Puncture characterization of rubber membranes," Theoretical and Applied Fracture Mechanics, vol. 42, 2004, pp. 25-33.
Nguyen, C.T. et al., "Mechanics and mechanisms of puncture of elastomer membranes," Journal of Materials Science, vol. 39, 2004, pp. 7361-7364.
Nguyen, Nam P. et al., "Effectiveness of the Cough Reflex in Patients with Aspiration Following Radiation for Head and Neck Cancer," Lung, vol. 185, 2007, pp. 243-248.
Nguyen, C. Thang et al., "Puncture of elastomer membranes by medical needles. Part I: Mechanisms," Int. J. Fract., vol. 155, 2009, pp. 75-81.
Nguyen, C. Thang et al., "Puncture of elastomer membranes by medical needles. Part II: Mechanics," Int. J. Fract., vol. 155, 2009, pp. 83-91.
Nishimura, T. et al., "Dental hygiene residential care in a 3-year dental hygiene education programme in Japan: towards dysphagia management based on dental hygiene process of care," Int. J. Dental Hygiene, vol. 5, 2007, pp. 145-150.
Okada, Sumiko SLP, MS et al., "What is the Chin-down Posture? A Questionnaire Survey of Speech Language Pathologists in Japan and the United States," Dysphagia, vol. 22, 2007, pp. 204-209.
Okubo, Paula de Carvalho Macedo Issa, MSc et al., "Clinical and Scintigraphic Assessment of Swallowing of Older Patients Admitted to a Tertiary Care Geriatric Ward," Dysphagia, vol. 23, 2008, pp. 1-6.
Okuda, Shinpei et al., "Morphologic Characteristics of Palatopharyngeal Muscle," Dysphagia, vol. 23, 2008, pp. 258-266.
Paine, Peter A. et al., "Modulation of Activity in Swallowing Motor Cortex Following Esophageal Acidification: A Functional Magnetic Resonance Imaging Study," Dysphagia, vol. 23, 2008, pp. 146-154.
Paliwal, Vimal K. et al., "Dysphagia in a Patient with Bilateral Medial Medullary Infarcts," Dysphagia, vol. 24, 2009, p. 349-353.
Pap, J-S. et al., "A robotic human masticatory system: kinematics simulations," Int. J. Intelligent Systems Technologies and Applications, vol. 1, Nos. ½, 2005, pp. 3-17.
Parcell, A.C. et al., "An upper arm model for simulated weightlessness," Acta. Physiol. Scand., vol. 169, 2000, pp. 47-54.
Park, Jin-Woo et al., "Effortful Swallowing Training Coupled with Electrical Stimulation Leads to an Increase in Hyoid Elevation During Swallowing," Dysphagia, vol. 24, 2009, pp. 296-301.
Park, Taeok et al., "Initiation and Duration of Laryngeal Closure During the Pharyngeal Swallow in Post-Stroke Patients," Dysphagia, vol. 25(3), 2010, published online Sep. 17, 2009, pp. 177-182.
Payne, Clare et al., "Consistently Inconsistent: Commercially Available Starch-Based Dysphagia Products," Dysphagia, vol. 26(1), 2011, published online Dec. 31, 2009, pp. 27-33.

Pedersen, Morten et al., "Miconazole and Miconazolenitrate Chewing Gum as Drug Delivery Systems—A Practical Application of Solid Dispersion Technique," Drug Development and Industrial Pharmacy, vol. 16(1), 1990, pp. 55-74.
Pedersen, Morten et al., "Miconazole Chewing Gum as a Drug Delivery System Test of Release Promoting Additives," Drug Development and Industrial Pharmacy, vol. 17(3), 1991, pp. 411-420.
Pettigrew, Catharine M. et al., "Dysphagia Evaluation Practices of Speech and Language Therapists in Ireland: Clinical Assessment and Instrumental Examination Decision-Making," Dysphagia, vol. 22, 2007, pp. 235-244.
Pichi, Barbara et al., "Rhabdomyoma of the Parapharyngeal Space Presenting with Dysphagia," Dysphagia, vol. 23, 2008, pp. 202-204.
Pitts, Teresa et al., "Voluntary Cough Production and Swallow Dysfunction in Parkinson's Disease," Dysphagia, vol. 23, 2008, pp. 297-301.
Platteaux, Nele et al., "Dysphagia in Head and Neck Cancer Patients Treated with Chemoradiotheraphy," Dysphagia, vol. 25(2), 2010, published online Aug. 27, 2009, pp. 139-152.
Plash, Octavia et al., "Effect of Gum Hardness on Chewing Pattern," Experimental Neurology, vol. 92, 1986, pp. 502-512.
Podnos, E. et al., "FEA analysis of silicone MCP implant," Journal of Biomechanics, vol. 39, 2006, pp. 1217-1226.
Power, Maxine L. et al., "Predicting Aspiration After Hemispheric Stroke from Timing Measures of Oropharyngeal Bolus Flow and Laryngeal Closure," Dysphagia, vol. 24, 2009, pp. 257-264.
Raadsheer, M.C. et al., "Human jaw muscle strength and size in relation to limb muscle strength and size," Eur. J. Oral Sci., vol. 112, 2004, pp. 398-405.
Regan, Julie et al., "Immediate Effects of Thermal-Tactile Stimulation on Timing of Swallow in Idiopathic Parkinson's Disease," Dysphagia, vol. 25(3), 2010, published online Aug. 26, 2009, pp. 207-215.
Reynolds, Eric W. et al., "Variability of Swallow-associated Sounds in Adults and Infants," Dysphagia, vol. 24, 2009, pp. 13-19.
Riecker, Axel et al., "Dysphagia Due to Unilateral Infarction in the Vascular Territory of the Anterior Insula," Dysphagia, vol. 24, 2009, pp. 114-118.
Roberts, D.F. et al., "Arm Strength and Body Dimensions," Human Biology, vol. 31:4, Dec. 1959, pp. 334-343.
Rogers, Sharon D. et al., "Cognitive Impairment and Effects on Upper Body Strenght of Adults With Dementia," J. Aging and Physical Activity, vol. 16, 2008, pp. 61-68.
Roubeau, Bernard PhD et al., "Use of Reaction Time in the Temporal Analysis of Normal Swallowing," Dysphagia, vol. 23, 2008, pp. 102-109.
Rydwik, E. et al., "Muscle strength testing with one repetition maximum in the arm/shoulder for people aged 75+—test-retest reliability," Clinical Rehabilitation, vol. 21, 2007, pp. 258-265.
Sakamoto, Kiwako et al., "Effect of Mastication on Human Brain Activity," Anti-Aging Medicine, vol. 7(13), 2010, pp. 153-160.
Sasaki, Clarence T. et al., "Comments on Selected Recent Dysphagia Literature," Dysphagia, vol. 19, 2004, pp. 60-63.
Sasaki, Clarence T. et al., "Comments on Selected Recent Dysphagia Literature," Dysphagia, vol. 22, 2007, pp. 161-164.
Sasaki, Clarence T. et al., "Comments on Selected Recent Dysphagia Literature," Dysphagia, vol. 22, 2007, pp. 276-279.
Sasaki, Clarence T. et al., "Comments on Selected Recent Dysphagia Literature," Dysphagia, vol. 22, 2007, pp. 335-339.
Sasaki, Clarence T. et al., "Comments on Selected Recent Dysphagia Literature," Dysphagia, vol. 23, 2008, pp. 208-212.
Sasaki, Clarence T. et al., "Comments on Selected Recent Dysphagia Literature," Dysphagia, vol. 23, 2008, pp. 213-218.
Sasaki, Clarence T. et al., "Comments on Selected Recent Dysphagia Literature," Dysphagia, vol. 23, 2008, pp. 413-419.
Sasaki, Clarence T. et al., "Comments on Selected Recent Dysphagia Literature," Dysphagia, vol. 24, 2009, pp. 119-125.
Sasaki, Clarence T. et al., "Comments on Selected Recent Dysphagia Literature," Dysphagia, vol. 24, 2009, pp. 249-255.
Sasaki, Clarence T. et al., "Comments on Selected Recent Dysphagia Literature," Dysphagia, vol. 24, 2009, pp. 362-367.
Sasaki, Clarence T. et al., "Comments on Selected Recent Dysphagia Literature," Dysphagia, vol. 24, 2009, pp. 441-446.

(56) References Cited

OTHER PUBLICATIONS

Sasaki, Clarence T. et al., "Comments on Selected Recent Dysphagia Literature," Dysphagia, vol. 25, 2010, pp. 73-78.
Sasaki, Clarence T. et al., "Comments on Selected Recent Dysphagia Literature," Dysphagia, vol. 25, 2010, pp. 265-270.
Schindler, Antonio et al., "Rehabilitative Management of Oropharyngeal Dysphagia in Acute Care Settings: Data from a Large Italian Teaching Hospital," Dysphagia, vol. 23, 2008, pp. 230-236.
Seo, Na Jin et al., "Effects of handle orientation, gloves, handle friction and elbow posture on maximum horizontal pull and push forces," Ergonomics, vol. 53, No. 1, Jan. 2010, pp. 92-101.
Seo, Han Gil et al., "Longitudinal Changes of the Swallowing Process in Subacute Stroke Patients with Aspiration," Dysphagia, vol. 26(1), 2011, published online Jan. 8, 2010, pp. 41-48.
Shaker, Reza, "Editorial: The 15$^{th}$ Anniversary of the Dysphagia Research Society and Establishment of the 'Endowment for the Future'," Dysphagia, vol. 23, 2008, p. 101.
Shimada, A. et al., "Measurement of dynamic bite force during mastication," Journal of Oral Rehabilitation, vol. 39, 2012, pp. 349-356.
Slavicek, G., "Human mastication," J. Stomat. Occ. Med., vol. 3, 2010, pp. 29-41.
Slavicek, G. et al., "Analysis of human mastication behavior: a new approach using planar calculations of fragmented chewing sequences," J. Stomat. Occ. Med., vol. 3, 2010, pp. 61-67.
Sokoloff, Alan J. et al., "Myosin Heavy-Chain Composition of the Human Hyoglossus Muscle," Dysphagia, vol. 25(2), 2010, published online Jun. 13, 2009, pp. 81-93.
Speyer, Renée et al., "Effects of Therapy in Oropharyngeal Dysphagia by Speech and Language Therapists: A Systematic Review," Dysphagia, vol. 25, 2010, pp. 40-65.
Strassburg, Julia et al., "Geometrical resolution limits and detection mechanisms in the oral cavity," Journal of Biomechanics, vol. 40, 2007, pp. 3533-3540.
Stec, Sebastian et al., "High-Resolution Esophageal Manometry with with ECG Monitoring for Management of Premature Ventricular Complexes-Associated Dysphagia," Dysphagia, vol. 25, 2010, pp. 66-69.
Steele, Catriona M. et al., "The Dynamics of Lingual-Mandibular Coordination During Liquid Swallowing," Dysphagia, vol. 23, 2008, pp. 33-46.
Stuart, Sheela et al., "Viscosity in Infant Dysphagia Management: Comparison of Viscosity of Thickened Liquids Used in Assessment and Thickened Liquids Used in Treatment," Dysphagia, vol. 24, 2009, pp. 412-422.
Stübgen, Joerg-Patrick, "Facioscapulohumeral Muscular Dystrophy: A Radiologic and Manometric Study of Pharynx and Esophagus," Dysphagia, vol. 23, 2008, pp. 341-347.
Suiter, Debra M. et al., "Clinical Utility of the 3-ounce Water Swallow Test," Dysphagia, vol. 23, 2008, pp. 244-250.
Tassinari, Carlo Alberto et al., "Biting Behavior, Aggression, and Seizures," Epillepsia, vol. 46(5), 2005, pp. 654-663.
Theurer, Julie A. et al., "Effects of Oropharyngeal Air-Pulse Stimulation on Swallowing in Healthy Older Adults," Dysphagia, vol. 24, 2009, pp. 302-313.
Thomis, M.A.I. et al., "Inheritance of static and dynamic arm strength and some of its determinants," Acta Physiol. Scand., vol. 163, 1998, pp. 59-71.
Thompson, C.L. et al., The Influence of Experimental Manipulations on Chewing Speed During In Vivo Laboratory Research in Tufted Capuchins (Cebus apella), American Journal of Physical Anthropology, vol. 145, 2011, pp. 402-414.
Thralow, Joan Ungerecht, BS, OTR et al., "Activities of daily living and cognitive levels of function in dementia," The American Journal of Alzheimer's Care and Related Disorders & Research, Sep./Oct. 1993, pp. 14-19.
Tippett, Donna C., Tracheotomy: Airway Management, Communication and Swallowing, 2$^{nd}$ ed., Edited by Eugene N. Myers and Jonas T. Johnson, Dysphagia, vol. 24, 2009, pp. 246-248.

Troche, Michelle S. et al., "Effects of Bolus Consistency on Timing and Safety of Swallow in Patients with Parkinson's Disease," Dysphagia, vol. 23, 2008, pp. 26-32.
Tsumori, Nobuaki et al., "Morphologic Characteristics of the Superior Pharyngeal Constrictor Muscle in Relation to the Function During Swallowing," Dysphagia, vol. 22, 2007, pp. 122-129.
Utanohara, Yuri et al., "Standard Values of Maximum Tongue Pressure Taken Using Newly Developed Disposable Tongue Pressure Measurement Device," Dysphagia, vol. 23, 2008, pp. 286-290.
Van der Bilt, A. et al., "Oral physiology and mastication," Physiology and Behavior, vol. 89, 2006, pp. 22-27.
Verin, E. et al., "Poststroke Dysphagia Rehabilitation by Repetitive Transcranial Magnetic Stimulation: A Noncontrolled Pilot Study," Dysphagia, vol. 24, 2009, pp. 204-210.
Wakasugi, Yoko et al., "Screening Test for Silent Aspiration at the Bedside," Dysphagia, vol. 23, 2008, pp. 364-370.
Wang, Jing et al., "Improved Adhesion of Silicone Rubber to Polyurethane by Surface Grafting," Journal of Applied Polymer Science, vol. 121, 2011, pp. 1245-1253.
Waller, Dave, "ARM's strength," Management Today, vol. 49, May 2007, 6 pages.
Warren-Forward, Helen et al., "Australian Speech-Language Pathologists' Knowledge and Practice of Radiation Protection While Performing Videofluoroscopic Swallowing Studies," Dysphagia, vol. 23, 2008, pp. 371-377.
Weers, Jeffry G. et al., "Design of fine particles for pulmonary drug delivery," Expert Opinion Drug Delivery, vol. 4(3), 2007, pp. 297-313.
Weijenberg, R.A.F. et al., "Mastication for the mind—The relationship between mastication and cognition in ageing and dementia," Neuroscience and Biobehavioral Reviews, vol. 35, 2011, pp. 483-497.
Wheeler, Karen M. PhD et al., "Surface Electromyographic Activity of the Submental Muscles During Swallow and Expiratory Pressure Threshold Training Tasks," Dysphagia, vol. 22, 2007, pp. 108-116.
Willett, Lisa L. MD et al., "An Unusual Cause of Chronic Cough," Case Report, J. Gen. Intern. Med., vol. 21, 2005, pp. C1-C3.
White, Kevin T. et al., "Fatigue Analysis Before and After Shaker Exercise: Physiologic Tool for Exercise Design," Dysphagia, vol. 23, 2008, pp. 385-391.
Woda, A. et al., "Development and validation of a mastication simulator," Journal of Biomechanics, vol. 43, 2010, pp. 1667-1673.
Wu, Xin et al., "Wide-mouthed Sacculation of the Esophagus: A Cause of Dysphagia after Radiation Therapy," Dysphagia, vol. 25(4), 2010, published online Mar. 4, 2010, pp. 341-344.
Yagi, Saiko et al., "Involvement of Sensory Input from Anterior Teeith in Deglutitive Tongue Function," Dysphagia, vol. 23, 2008, pp. 221-229.
Yang, Feng et al., "An algorithm for simulating human arm movement considering the comfort level," Simulation Modeling Practice and Theory, vol. 13, 2005, pp. 437-449.
Yokoi, Teruo et al., "Investigation of Eating Actions of People with Dementia From the Viewpoint of Self-Awareness," American Journal of Alzheimer's Disease and Other Dementias, vol. 27, 2012, pp. 228-237.
Youmans, Scott R. et al., "Differences in Tongue Strength Across Age and Gender: Is There a Diminished Strength Reserve?" Dysphagia, vol. 24, 2009, pp. 57-65.
Zimmerman, Jack E. et al., "Swallowing Dysfunction in Acutely Ill Patients," Physical Therapy, vol. 61, No. 12, Dec. 1981, pp. 1755-1763.
Živko-Babić, J. et al., "Bite Force in Subjects with Complete Dentition," Coll. Antropol., vol. 26, 2002, pp. 293-302.
Abella, Amanda et al., "How to Reuse Daily Contact Lenses," eHow, http://www.ehow.com/how_7455972_reuse-daily-contact-lenses.html, reviewed Sep. 2012, retrieved online Nov. 21, 2013, 2 pages.
Arnold, Dr. M.A. (Toby), "Arnold's Glossary of Anatomy," The University of Sydney, Jun. 2010, 49 pages.
Bishop, Eric et al., "Multi-Component Molding of Liquid Silicone Rubber Over Thermoplastics," Medical Silicone Conference, Anaheim, Nov. 3-4, 2010, 54 pages.

(56) References Cited

OTHER PUBLICATIONS

Chan, Simon Y.P. et al., "Changes in Arterial Oxygen Saturation ($SaO_2$) Before, During, and After Meals in Stroke Patients in a Rehabilitation Setting," Dysphagia, vol. 24, 2009, pp. 77-82.

Constantino, Paul J. et al., "Tooth chipping can reveal the diet and bite force of fossil hominins," Biol. Lett., vol. 6, 2010, pp. 826-829.

Davies, C.N., "Inhaled Particles," Edited by W.H. Walton, 1971, pp. xvi+viii+1090, Two volumes, Unwin Brothers, Old Woking, Book Reviews, pp. 213-221.

Demura, Shinich et al., "The Difference in Output Properties Between Dominant and Nondominant Limbs as Measured by Various Muscle Function Tests," Journal of Strength and Conditioning Research, vol. 24, No. 10, pp. 2816-2820.

Dolnikov, Y.I., "Experimental research on the movements in the large joint of arm," Central Scientific Research Institute of Prosthetics and Orthopedic Appliances, 1964, 13 pages.

Duarte Silva, Luiz Filipe et al., "Are There Any Differences Between Nutcracker Esophagus With and Without Reflux?," Dysphagia, vol. 22, 2007, pp. 245-250.

Ergun, Gulchin A. MD, "Swallowing Disorders and Dysphagia," Chapters 1 and 2, date unknown but prior to at least Mar. 28, 2013, 13 pages.

Etter, Jean-Francois, "Electronic cigarettes: a survery of users," BMC Public Health, vol. 10, 2010, 7 pages.

Frank, F.C. et al., "On the theory of Hertzian fracture," Proceedings of the Royal Society of London, Series A, Mathematical and Physical Sciences, © 1967, pp. 291-306.

Frunza, Mihai Catalin et al., "Cusp radius measurement through digital image analysis," Acta Odontologica Scandinavica, vol. 71, 2013, pp. 236-240.

Goldberg, Jon A., "Viscoelastic Properties of Silicone, Polysulfide, and Polyether Impression Materials," Journal of Dental Research, vol. 5, No. 53, 1974, pp. 1033-1039.

Higgins, Johanne et al., "The effect of a task-oriented intervention on arm function in people with stroke: a randomized controlled trial," Clinical Rehabilitation, vol. 20, 2006, pp. 296-310.

Hutchings, Scott C., "Oral processing of heterogeneous foods," A thesis presented in partial fulfillment of the requirements for the Ph.D. in Food Science at Massey Univ., NZ, 2011, 266 pages.

Hutchings, Scott C. et al., "Mastication of heterogeneous foods: Peanuts inside two different food matrices," Food Quality and Preferences, vol. 22, 2011, pp. 332-339.

Hutchinson, Matt et al., "A Brief Atlas of the Human Body," Copyright 1989, Pearson Education, Inc. publishing as Benjamin Cummings, San Francisco, CA, 28 pages.

Imai, E. et al., "Effect of Physical Properties of Food Particles on the Degree of Graininess Perceived in the Mouth," Journal of Texture Studies, vol. 30, 1999, pp. 59-88.

Klompen, Edwin TJ, "Mechanical properties of solid polymers—Consultative modeling of long and short term behavior," Technische Universiteit Eindhoven, 2005, 155 pages.

Koolstra, J.H. et al., "Application and Validation of a Three-Dimensional Mathematical Model of the Human Masticatory System In Vivo," J. Biomechanics, vol. 25, No. 2, 1992, pp. 175-187.

Koolstra, J.H. et al., Three-dimensional dynamical capabilities of the human masticatory muscles, Journal of Biomechanics, vol. 32, 1999, pp. 145-152.

Kothari, M. et al., "Influence of the ability to roll the tongue and tongue-training parameters on oral motor performance and learning," Archives of Oral Biology, vol. 56, 2011, pp. 1419-1423.

Kothari, M. et al., "Force and complexity of tongue task training influences behavioral measures of motor learning," European Journal of Oral Sciences, vol. 119, 2011, pp. 1-8.

Kumar, Shrawan, "Muscle Strength," CRS Press, © 2004, ISBN 0-415-36953-3, 24 pages.

Langdon, Claire, "Dysphagia and Respiratory Infections in Acute Ischemic Stroke," Acute Ischemic Stroke, Jan. 2012, pp. 80-100.

Larian, Babak, M.D., "Swallowing Problems (Dysphagia)," http://www.larianmd.com/areas-of-practice/voice-swallowing.html, © 2012, retrieved from the Internet Dec. 13, 2013, 5 pages.

Lawn, B.R., "Partial cone crack formation in a brittle material loaded with a sliding spherical indenter," Proceedings of the Royal Society of London, Series A, Mathematical and Physical Sciences, © 1967, pp. 307-316.

Liedberg, Birgitta, DDS et al., "Oral Bolus Kneading and Shaping Measured with Chewing Gum," Dysphagia, vol. 10, 1995, pp. 101-106.

Litonjua, Luis A. et al., "An assessment of stress analyses in the theory of abfraction," Bio-Medical Materials and Engineering, vol. 14, 2001, pp. 311-321.

Lowell, Soren Y. et al., "Sensory stimulation activates both motor and sensory components of the swallowing system," NeuroImage, vol. 42, 2008, pp. 285-295.

Miah, Khosru, "Silicone Hydrogels: manufacturing the future today," Acryate Research & Development Ltd., Technical Paper #A843001, Oct. 2006, 1 page.

Miner, John, "Chewing Gum It's Good for You," London Free Press, published prior to at least Mar. 28, 2013, 1 page.

Mizuko, Mark et al., "Identification of Swallowing Patterns Associated with Dysphagia," University of Minnesota Duluth, http://www.d.umn.edu/csd/video/swallowing.htm, © 1998, last modified Mar. 25, 2011, retrieved from the Internet Dec. 13, 2013, 3 pages.

Mountain, Gary et al., "Bite force measurement in children with primary dentition," International Journal of Pediatric Dentistry, vol. 21, 2011, pp. 112-118.

Naitove, Matthew H., "Do's and Don'ts for Overmolding Liquid Silicone onto Thermoplastics," Plastics Technology, vol. 56(3), Mar. 2010, pp. 26-27.

Newman, Anne B., MD, MPH et al., "Strength and Muscle Quality in a Well-Functioning Cohort of Older Adults: The Heath, Aging and Body Composition Study," JAGS, vol. 51, 2003, pp. 323-330.

Nishinari, Katsuyoshi, "Rheology, Food Texture and Mastication," Journal of Texture Studies, vol. 35, 2004, pp. 113-124.

Nohara, Kanji DDS, PhD et al., "Power Spectra Analysis of Levator Veli Palatini Muscle Electromyogram During Velopharyngeal Closure for Swallowing, Speech, and Blowing," Dysphagia, vol. 22, 2007, pp. 135-139.

Paik, Nam-Jong, "Dysphagia," http://www.emedicine.medscape.com/article/324096-overview, May 29, 2012, retrieved from the Internet Dec. 13, 2013, 5 pages.

Pileicikiene, Gaivile et al, "The Human Masticatory System From a Biomechanical Perspective: A Review," Stomatologija, Baltic Dental and Maxillofacial Journal, vol. 6, 2004, pp. 81-84.

Rosiak, Janusz M. et al., "Radiation Formation of Hydrogels for Biomedical Application," Radiation Physics and Chemistry, vol. 46, Issue 2, Aug. 1995, pp. 161-168.

Roylance, David, "Engineering Viscoelasticity," Dept. of Materials Science and Engineering, MIT, Oct. 2001, 37 pages.

Saitoh, Eiichi, MD, DMSc et al., "Chewing and Food Consistency: Effects on Bolus Transport and Swallow Initiation," Dysphagia, vol. 22, 2007, pp. 100-107.

Schimmel, M. et al., "Masticatory Function and Bite Force in Stroke Patients," Journal of Dental Research, vol. 90, 2011, pp. 230-234.

Simon, Josh, "Effects of Testing Parameters on Pinch Test Results for Hydrophilic Coatings," Biocoat, Inc. Slideshow Presentation, Published prior to at least Mar. 28, 2013, 36 pages.

Simon, Josh, "Hydrophilic Coatings: Consideration for product development and choice," Technical White Paper, www.biocoat.com, published prior to at least Mar. 28, 2013, 8 pages.

Smith, Marianne et al., "Behaviors Associated with Dementia," AJN, vol. 105, No. 7, 2005, pp. 40-52.

Sothmann, M.S. et al., "Performing requirements of physically strenuous occupations: validating minimum standards for muscular strength and endurance," Ergonomics, vol. 47, No. 8, Jun. 2004, pp. 864-875.

Tighe, Brian et al., "Silicone hydrogels—What are they and how should they be used in everyday practice," Contact Lens Monthly, vol. 218, No. 5726, Nov. 1999, pp. 31-35.

Unknown author, "Oral-B® Indicator® Toothbrush," http://www.dentalcare.com/en-US/oral-b-crest-professional-products/category/manual-toothbrushes/oralb-indicator.aspx, 2002, retrieved online Nov. 21, 2013, 1 page.

(56) References Cited

OTHER PUBLICATIONS

Unknown author, "Chewing Gum (How Products are Made)," Gale Cengage, How Products are Made, www.enotes.com/topics/chewing-gum, 2002, retrieved online Nov. 21, 2013, 6 pages.
Unknown author, "Safety Razor (How Products are Made)," Gale Cengage, How Products are Made, www.enotes.com/topics/safety-razor, 2002, retrieved online Nov. 21, 2013, 6 pages.
Unknown author, "Socioeconomics," Wikipedia, http://en.wikipedia.org/wiki/Socioeconomics, reviewed Sep. 1012, retrieved online Nov. 21, 2013, 4 pages.
Unknown author, "PDI Lemon Glycerin Swabsticks," © 2009 Quick Medical—Medical Equipment and Supplies, www.quickmedical.com/pdi/lemon-glycerin-swabstikcs.html, retrieved online Nov. 22, 2013, 2 pages.
Unknown author, "Flavored Tongue Depressors," © 2013, Super Duper® Publications, Greenville, SC, www.superduper.com/products/view.aspx?stid=171, retrieved online Nov. 22, 2013, 2 pages.
Unknown author, "Specification for 'Babies' elastomeric feeding bottle teats'," British Standard, BSi, BS 7368:1990, © 1990, 10 pages.
Unknown author, "Dental implants—Guidelines for developing dental implants," Technical Report, International Organization for Standardization (ISO) TR11175, Aug. 1993, 8 pages.
Unknown author, "Flavored Medical Gloves," Southpaw Enterprises®, Inc., www.southpawenterprises.com/OralMotor/FlavoredMedicalGloves.asp, retrieved online Nov. 26, 2013, 1 page.
Unknown author, "Commercial Life Science Products & Services," SAFC, © 2013 Sigma-Aldrich Co. LLC, www.sigmaaldrich.com/safc.html, retrieved online Nov. 26, 2013, 2 pages.
Unknown author, "Dentistry—Implants—Dynamic fatigue test for endosseous dental implants," International Standard, International Organization for Standardization (ISO) 14801, Nov. 2007, 13 pages.
Unknown author, "Roles of Speech-Language Pathologists in Swallowing and Feeding Disorders: Technical Report," American Speech-Language-Hearing Association, DOI 10.1044/policy. TR2001-00150, Dysphagia Document Review and Working Group, © 2001, 31 pages.
Unknown author, "Human Integration Design Handbook (HIDH)," NASA Handbook, Baseline, Washington, DC, Jan. 2010, 1,136 pages.
Unknown author, "Child use and care articles—Soother holder—Safety requirements and test methods," British Standard, BSi, BS EN 12586:2007, © 2011, European Committee for Standardization, 56 pages.
Unknown author, "Liquid Silicones Boast High Tear Strength," Plastics Technology, vol. 53(11), Nov. 2007, p. 29.
Unknown author, "Dysphagia—The trouble with swallowing," Mayo Clinic Health Letter, vol. 28, No. 10, Oct. 2010, 3 pages.
Unknown author, "Standard Practice for Conditioning Plastics for Testing," ASTM International, Designation: D618-08, Mar. 2011, 4 pages.
Unknown author, "Standard Test Method for Tensile Properties of Plastics," ASTM International, Designation: D638-10, Mar. 2011, 16 pages.
Unknown author, "Standard Test Method for Tear Strength of Conventional Vulcanized Rubber and Thermoplastic Elastomers," ASTM International, Designation: D624-00, Mar. 2011, 9 pages.
Unknown author, "Standard Test Method for Compressive Properties of Rigid Plastics," ASTM International, Designation: D695-10, Mar. 2011, 7 pages.
Unknown author, "Standard Test Methods for Flexural Properties of Unreinforced and Reinforced Plastics and Electrical Insulating Materials," ASTM International, Designation: D790-10, Mar. 2011, 11 pages.
Unknown author, "Standard Test Method for Tensile Properties of Thin Plastic Sheeting," ASTM International, Designation: D882-10, Mar. 2011, 16 pages.
Unknown author, "Standard Test Method for Bearing Strength of Plastics," ASTM International, Designation: D953-10, Mar. 2011, 6 pages.
Unknown author, "Standard Test Method for Tear Resistance (Graves Tear) of Plastic Film and Sheeting," ASTM International, Designation: D1004-09, Mar. 2011, 4 pages.

Unknown author, "Standard Terminology Relating to Rubber," ASTM International, Designation: D1566-10, Mar. 2011, 15 pages.
Unknown author, "Standard Test Method for Propagation Tear Resistance of Plastic Film and Thin Sheeting by Pendulum Method," ASTM International, Designation: D1922-09, Mar. 2011, 7 pages.
Unknown author, "Standard Test Method for Tear-Propagation Resistance (Trouser Tear) of Plastic Film and Thin Sheeting by a Single-Tear Method," ASTM International, Designation: D1938-08, Mar. 2011, 4 pages.
Unknown author, "Standard Method for Puncture-Propagation Tear Resistance of Plastic Film and Thin Sheeting," ASTM International, Designation: D2582-09, Mar. 2011, 5 pages.
Unknown author, "Standard Specification for Poly(Vinyl Chloride) (PVC) Plastic Drain, Waste, and Vent Pipe and Fittings," ASTM International, Designation: D2665-10, Mar. 2011, 7 pages.
Unknown author, "Standard Test Method for Strength Properties of Adhesively Bonded Plastic Lap-Shear Sandwich Joints in Shear by Tension Loading," ASTM International, Designation: D3164-03, Mar. 2011, 4 pages.
Unknown author, "Standard Practice for Injection Molding Test Specimens of Thermoplastics Molding and Extrusion Materials," ASTM International, Designation: D3641-10a, Mar. 2011, 9 pages.
Unknown author, "Standard Test Method for Rubber Property-Extension Cycling Fatigue," ASTM International, Designation: D4482-07, Mar. 2011, 9 pages.
Unknown author, "Standard Test Method for Chip Impact Strength of Plastics," ASTM International, Designation: D4508-10, Mar. 2011, 6 pages.
Unknown author, "Standard Practice for Compression Molding Thermoplastic Materials into Test Specimens, Plaques, or Sheets," ASTM International, Designation: D4703-10a, Mar. 2011, 12 pages.
Unknown author, "Standard Test Methods for Rubber-Measurement of Processing Properties Using Capillary Rheometry," ASTM International, Designation: D5099-08, Mar. 2011, 8 pages.
Unknown author, "Standard Practice for Determining Physical Properties of Fabrics, Yarns, and Sewing Thread Used in Inflatable Restraints," ASTM International, Designation: D5446-08, 5 pages.
Unknown author, "Standard Test Method for Determining the Charpy Impact Resistance of Notched Specimens of Plastics," ASTM International, Designation: D6110-10, Mar. 2011, 17 pages.
Unknown author, "Standard Practice for Cutting Film and Sheeting Test Specimens," ASTM International, Designation: D6287-09, Mar. 2011, 3 pages.
Unknown author, "Standard Test Method for High Speed Puncture Properties of Plastic Films Using Load and Displacement Sensors," ASTM International, Designation: D7192-10, Mar. 2011, 8 pages.
Unknown author, "Standard Practice for Strain-Controlled Fatigue Testing," ASTM International, Designation: E606-04, Mar. 2011, 16 pages.
Unknown author, "Standard Test Method for Measurement of Fatigue Crack Growth Rates," ASTM International, Designation: E647-08, Mar. 2011, 45 pages.
Unknown author, "Standard Guide for Time-Intensity Evaluation of Sensory Attributes," ASTM International, Designation: E1909-97, Mar. 2011, 15 pages.
Unknown author, "Standard Test Method for Odor or Flavor Transfer or Both from Rigid Polymeric Packaging," ASTM International, Designation: E2609-08, Mar. 2011, 10 pages.
Unknown author, "Standard Classification for Vinyl Chloride Plastics Used in Biomedical Application," ASTM International, Designation: F665-09, Mar. 2011, 4 pages.
Unknown author, "Standard Practice for Care and Use of Athletic Mouth Protectors," ASTM International, Designation: F697-00, Mar. 2011, 2 pages.
Unknown author, "Standard Specification for Poly(Vinyl Chloride) (PVC) Plastic Drain, Waste, and Vent (DWV) Pipe and Fittings Having Post-Industrial Recycle Content," ASTM International, Designation: F2390-07, Mar. 2011, 7 pages.
Unknown author, "Standard Guide for Silicone Elastomers, Gels, and Foams Used in Medical Applications Part II—Crosslinking and Fabrication," ASTM International, Designation: F2042-00, Mar. 2011, 7 pages.
Unknown author, "Standard Guide for Developing and Selecting Wear Tests," ASTM International, Designation: G190-06, Mar. 2011, 5 pages.

(56) References Cited

OTHER PUBLICATIONS

Unknown author, "Guidance for Industry and Food and Drug Administration Staff—Factors to Consider When Making Benefit-Risk Determinations in Medical Device Premarket Approval and *De Novo* Classifications," DHHS, FDA, Centers for Devices and Radiological Health, Centers for Biological Evaluation and Research, Mar. 2012, 55 pages.
Unknown author, "Title 21—Food and Drugs—Chapter 1—Food and Drug Administration—Department of Health and Human Services—Subchapter B—Food for Human Consumption (Continued)," Code of Federal Regulations, Title 21, vol. 3, Revised as of Apr. 1, 2011.
Unknown author, "4a Humanscale™ Human Strenght," Designed by Henry Dreyfuss Associates, published prior to at least Mar. 28, 2013, 5 pages.
Unknown author, "Lubricious Hydrophilic Coatings for Medical Devices," Biocoat Incorporated. www.biocoat.com, © 2013, retrieved online Nov. 26, 2013, 2 pages.
Unknown author, "Contolled Surface, Controlled Process," Plasma Technology Systems, www.plasmatechsystems.com, © 2013, retrieved online Nov. 26, 2013, 1 page.
Unknown author, "Ice Finger," AliMed, www.alimed.com/ice-finger.html, © 2013, retrieved online Nov. 26, 2013, 1 page.
Unknown author, Dysphagia Message Board, www.healthboards.com/boards/dysphagia, © 1998-2013, retrieved online Nov. 26, 2013, 2 pages.
Unknown author, Oral-B® Indicator Toothbrush, Oral-B, www.oralb.com/products/indicator-toothbrush.aspx, retrieved online Nov. 26, 2013, 1 page.
Unknown author, "Reducing Disability From Stroke in the Great Lakes Region," National Association of Chronic Disease Directors, published prior to at least Mar. 28, 2013, 1 page.
Unknown author, "Overmolding Guide," GLS Corporation, © 2004, 18 pages.
Unknown author, Oral Swab 6 information sheet, www.punktura.ro/medicalsupply/Oral_Swab_6_inch_Plastic_Individually_Wrapped_Flavored_Latex_Free_Case.460705985.php, published prior to at least Mar. 28, 2013, 1 page.
Unknown author, "Child use and care articles—Drinking equipment—Part 1: General and mechanical requirements and tests," European Standard EN 14350-1, European Committee for Standardization, Aug. 2004, 24 pages.
Unknown author, "Child use and care articles—Drinking equipment—Part 2: Chemical requirements and tests," European Standard EN 14350-2, European Committee for Standardization, Aug. 2004, 21 pages.
Unknown author, "Methods for Sampling and Testing Gelatine (physical and chemical methods)," BSI, British Standards Institution, BS 757 : 1975, © 1975, 34 pages.
Unknown author, "Child use and care articles—Soothers for babies and young children—Part 1: General Safety requirements and product information," BSI, British Standards Institution, BS EN 1400-1:2002, Oct. 2002, 30 pages.
Unknown author, "Child use and care articles—Soothers for babies and young children—Part 2: Mechanical requirements and tests," BSI, British Standards Institution, BS EN 1400-2:2002, Oct. 2002, 30 pages.
Unknown author, "Child use and care articles—Soothers for babies and young children—Part 3: Chemical requirements and tests," BSI, British Standards Institution, BS EN 1400-3:2002, Oct. 2002, 18 pages.
Unknown author, "The Design Guide for Bonding Rubber and Thermoplastic Elastomers," Locite, vol. 2 2/05, Henkel Corporation, 2005, 78 pages.
Unknown author, "Lemon Glycerin Swabsticks," Medline Industries, Inc., http://www.medline.com/sku/item/MDPMD090600, retrieved from the Internet on Dec. 13, 2013, published prior to at least Mar. 28, 2013, 1 page.
Unknown author, ARK's Oro-Navigator™, ARK Therapeutic Services, Inc., http://www.arktherapeutic.com/ONAVIxxAR.html, retrieved from the Internet on Dec. 13, 2013, published prior to at least Mar. 28, 2013, 2 pages.
Unknown author, ARK's DnZ-Vibe®, ARK Therapeutic Services, Inc., http://www.arktherapeutic.com/DnZV100CAR.html, retrieved from the Internet on Dec. 13, 2013, published prior to at least Mar. 28, 2013, 3 pages.
Unknown author, ARK's Bite-n-Chew Tip Combo, ARK Therapeutic Services, Inc., http://www.arktherapeutic.com/ZVBC400SAR.html, retrieved from the Internet on Dec. 13, 2013, published prior to at least Mar. 28, 2013, 2 pages.
Unknown author, "Chewy Tubes," http://chewytubes.com/products/chewy-tubes/, retrieved from the Internet on Dec. 13, 2013, published prior to at least Mar. 28, 2013, 2 pages.
Unknown author, "How TheraSIP Works," TheraSIP Swallowing Treatment, http://therasip.com/index.cfm/fuseaction/howitworks.index, retrieved from the Internet on Dec. 13, 2013, © 2010, 3 pages.
Unknown author, "Lab: Testing for the Presence of Organic Compounds—'Spit & Chew'," National Association of Chronic Disease Directors, published prior to at least Mar. 28, 2013, 4 pages.
Unknown author, "Statement on Standard Practice for Infection Prevention and Control Instruments for Tracheal Intubation," Committee of Origin: Committee on Quality Management and Departmental Administration (QMDA), Oct. 20, 2010, 1 page.
Unknown author, "Pharynx and Larynx," http://www.emory.edu/ANATOMY/AnatomyManual/pharynx.html, retrieved from the Internet on Dec. 13, 2013, published prior to at least Mar. 28, 2013, 8 pages.
Unknown author, "Identification of Swallowing Patterns Associated with Dysphagia," UM Technology Enhanced Learning Project Description, http://www.d.umn.edu/csd/video/nhoney.htm, retrieved from the Internet on Dec. 13, 2013, published prior to at least Mar. 28, 2013, 2 pages.
Unknown author, picture of Esophagus, http://www.meddean.luc.edu/lumen/meded/Radio/curriculum/ENT, retrieved from the Internet on Dec. 13, 2013, published prior to at least Mar. 28, 2013, 1 page.
Unknown author, "Deglutition," Netter Medical Images, http://www.netterimages.com/images/2125.htm, © 2005-2012, Elsevier, retrieved from the Internet on Dec. 13, 2013, 2 pages.
Van der Bilt, A. et al., "Oral physiology and mastication," Physiology & Behavior, vol. 89, 2006, pp. 22-27.
Various authors, "Society for Oral Physiology—Store Kro Group," Twenty-Second Biennial Meeting, Jun. 7-10, 2001, Lugano, Switzerland, Abstract of Selected Presentations, Journal of Oral Rehabilitation, vol. 29, 2002, pp. 872-889.
Various authors, "Dysphagia Research Society," Seventeenth Annual Dysphagia Research Society Meeting, Mar. 4-7, 2009, New Orleans, Dysphagia, vol. 24, 2009, pp. 449-460.
Viana Silva, Ana Cristina et al., "A Scintigraphic Study of Oral, Pharyngeal, and Esophageal Transit in Patients with Stroke," Dysphagia, vol. 23, 2008, pp. 165-171.
Voss, Sarah J., "Two-Shot Silicone—Thermoplastic Medical Molding," Saint-Gobain Performance Plastics, published prior to at least Mar. 28, 2013, 7 pages.
Xu, Weilang et al., "Mastication Robots—Biological Inspiration to Implementation," © 2010, Springer-Verlag, Berlin, Heidelberg, ISBN 978-3-54083902-3, DOI 10.1007/978-3-540-93903-0, Library of Congress Control No. 2010928433, 301 pages.
Yang, Xinghao et al., "Release Kinetics of Catechins from Chewing Gum," Journal of Pharmaceutical Sciences, vol. 93, No. 2, Feb. 2004, pp. 293-299.
Yoshida, Ryo, "Self-Oscillating Gel as Novel Biomimetic Materials," Proceedings of the 14th International Symposium on Recent Advances in Drug Delivery Systems, Journal of Controlled Release, vol. 140, Issue 3, Dec. 2009, pp. 186-193.
International Search Report and Written Opinion of the International Searching Authority for International Application No. PCT/IB2013/000568, dated.
Notification of Reason for Rejection from Japanese Application No. 2011-504558, dated Jun. 4, 2013, 4 pages.

\* cited by examiner

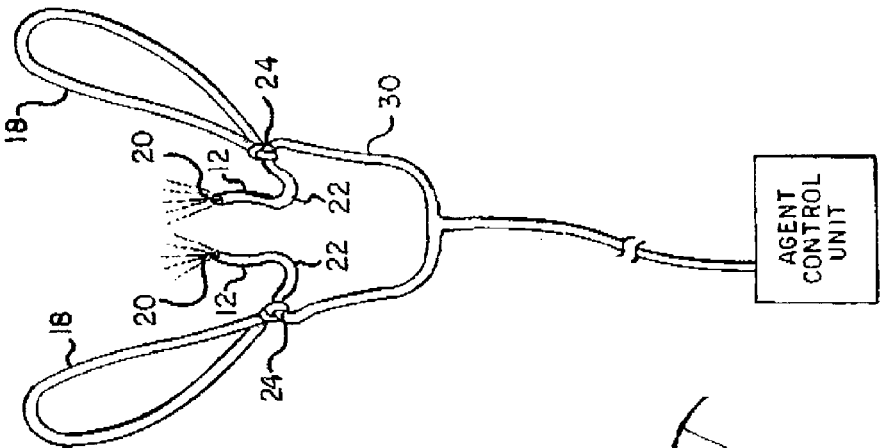
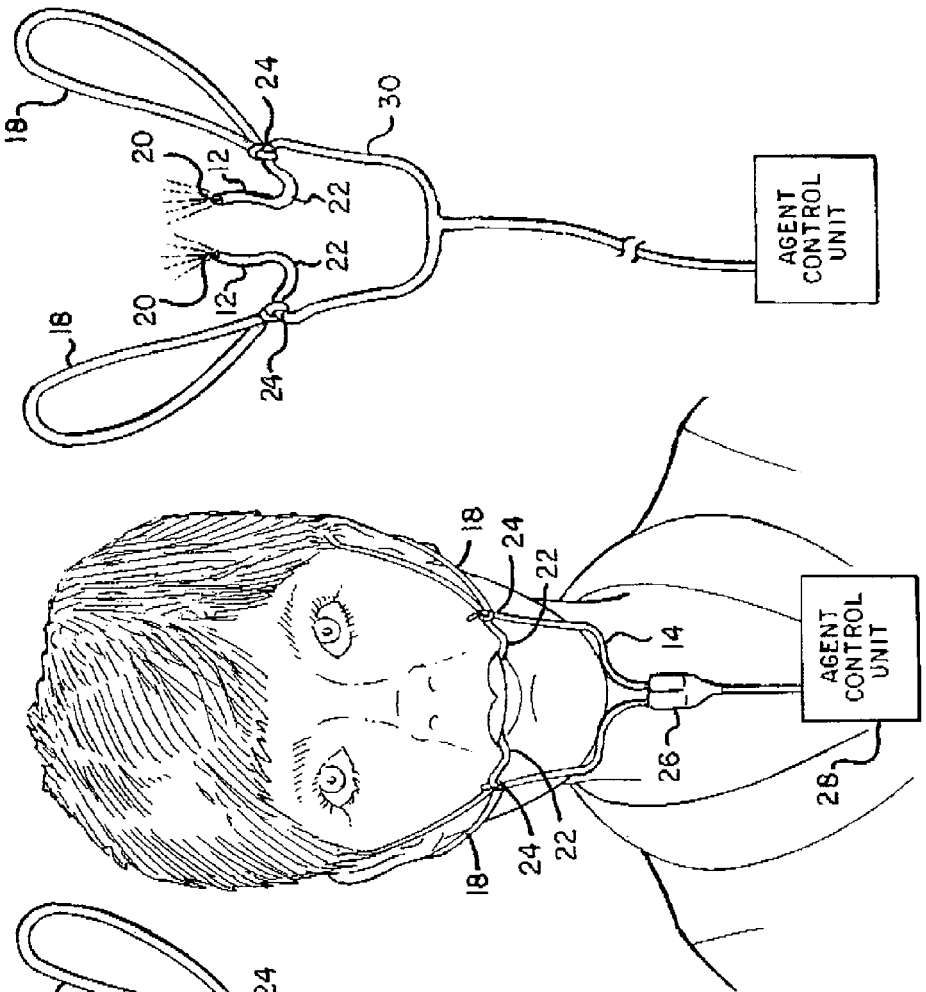
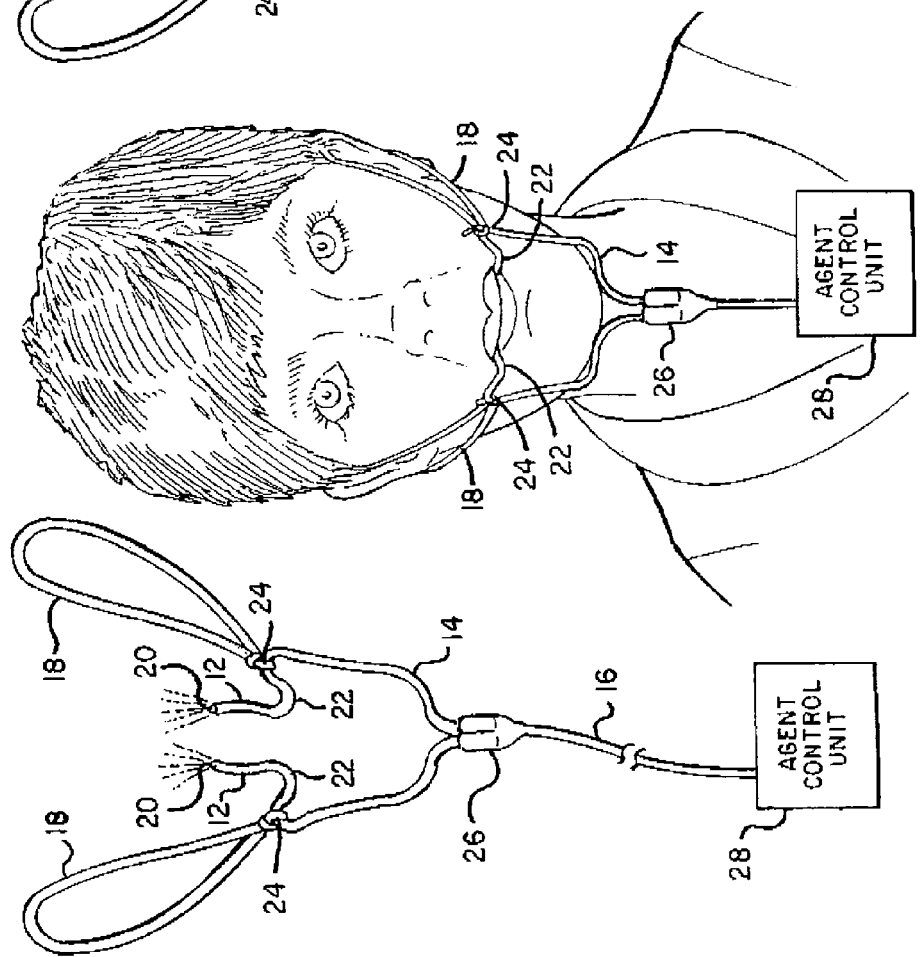

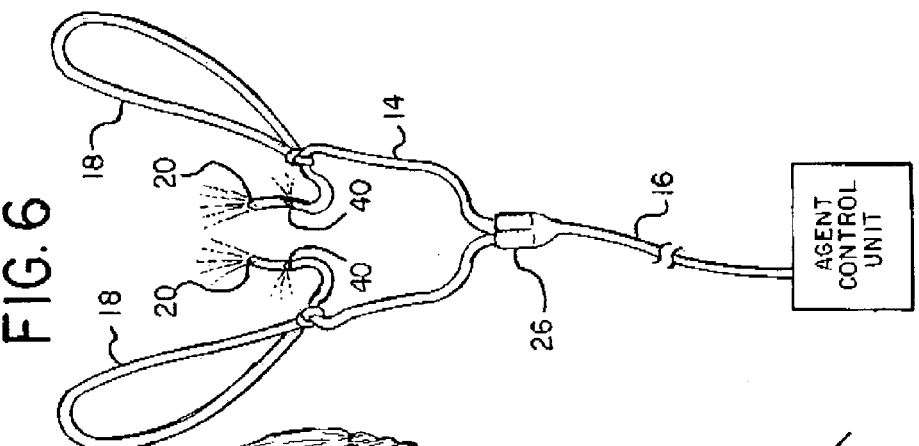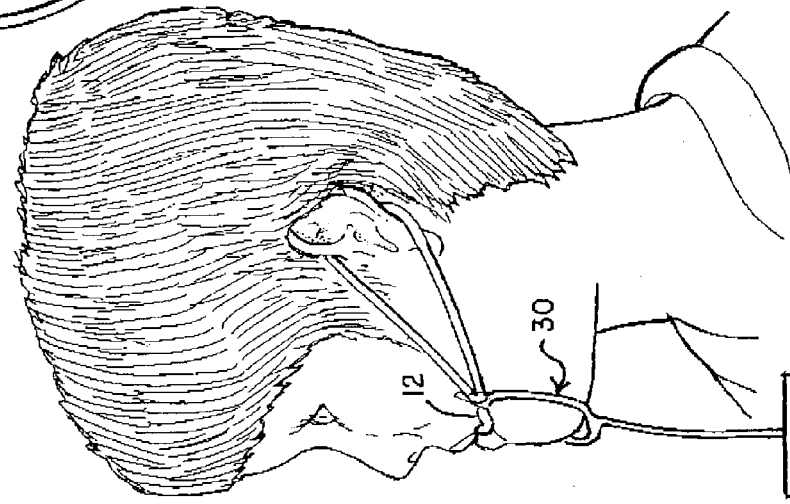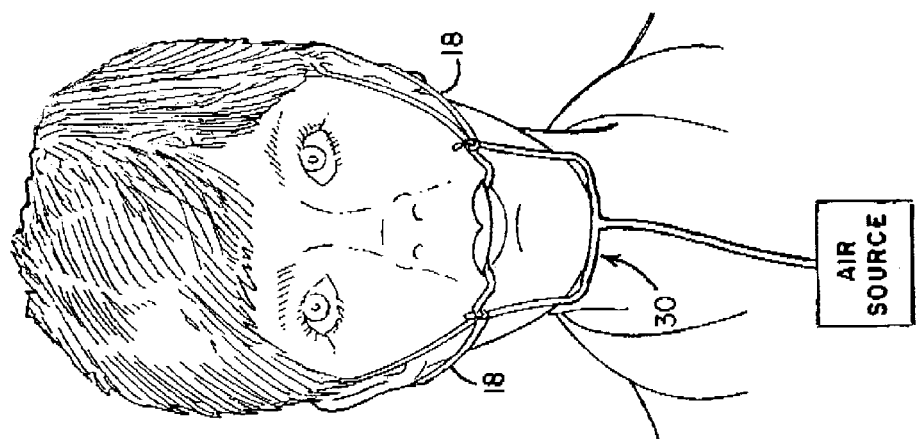

AIR-PULSE TRAIN DURATION VS SHAM

EFFECT OF AIR-PULSE AMPLITUDE

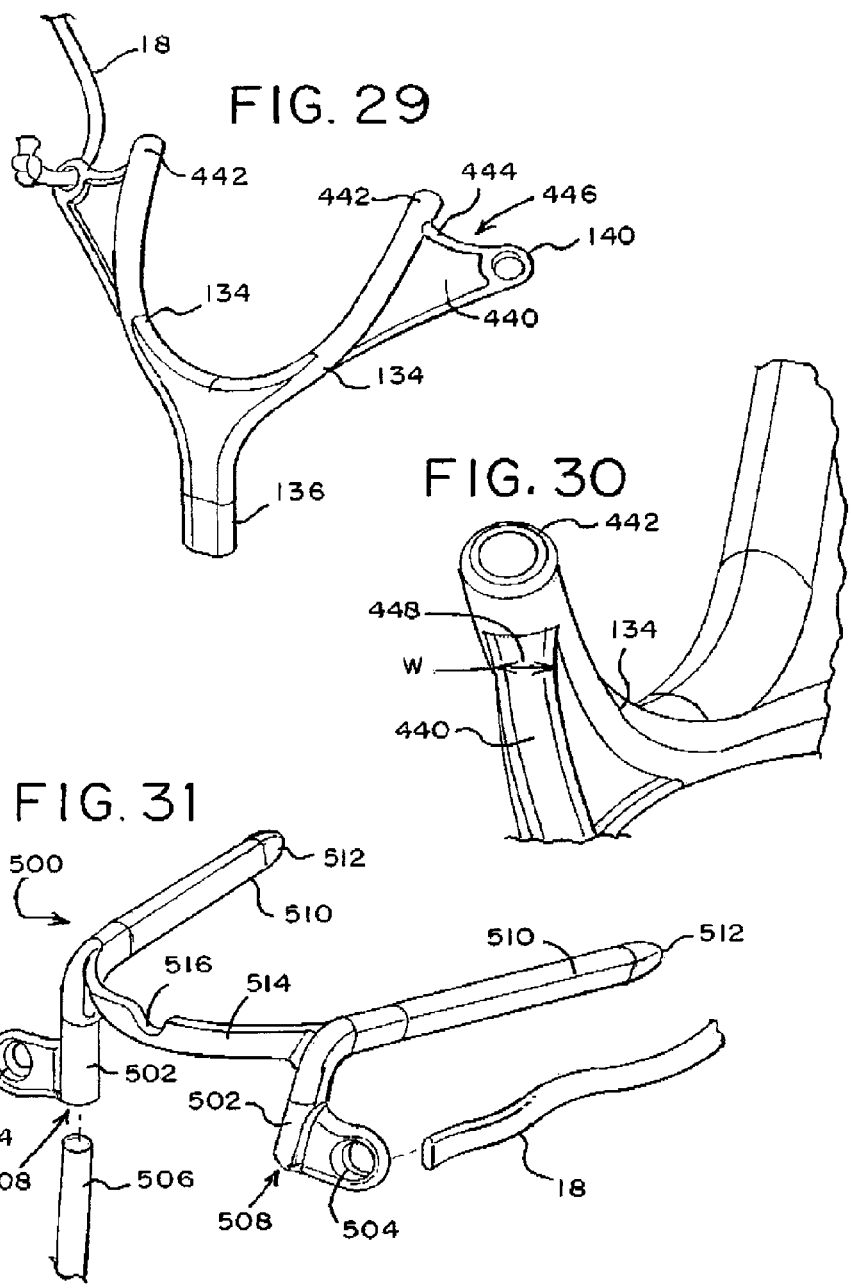

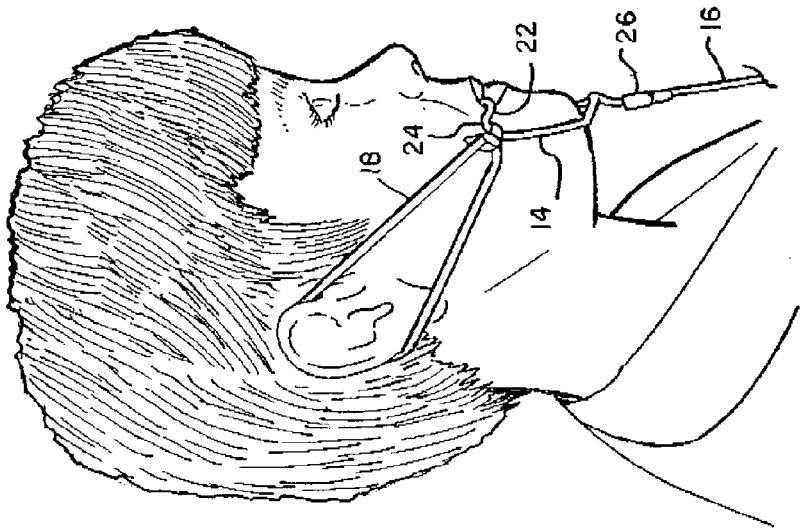
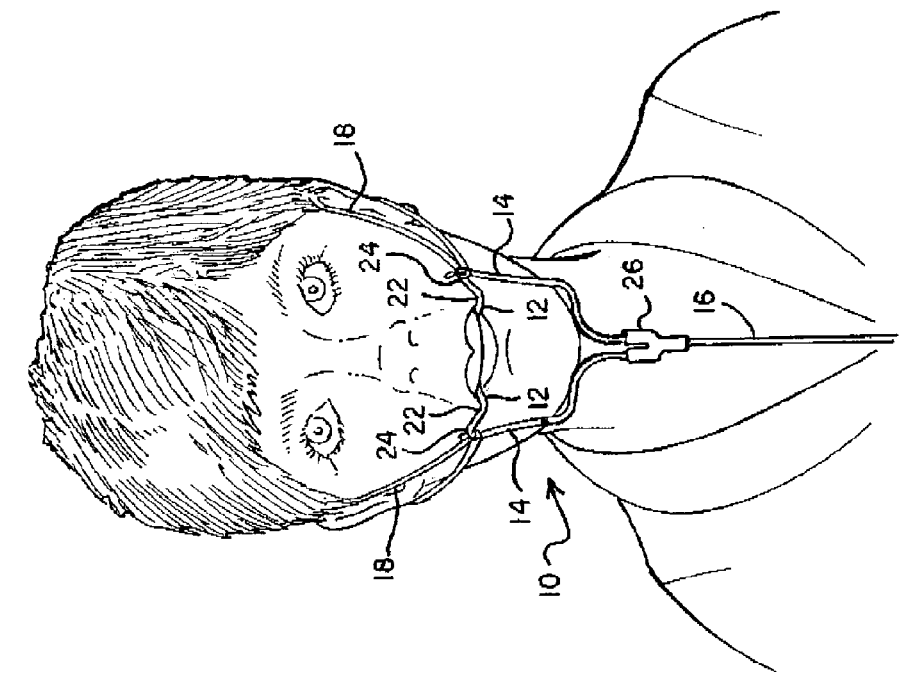

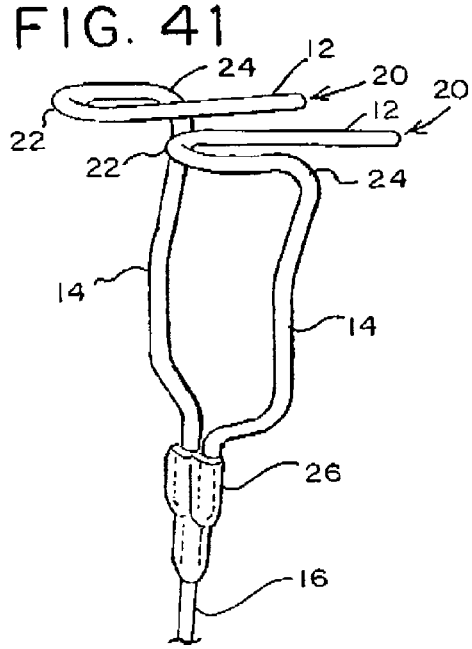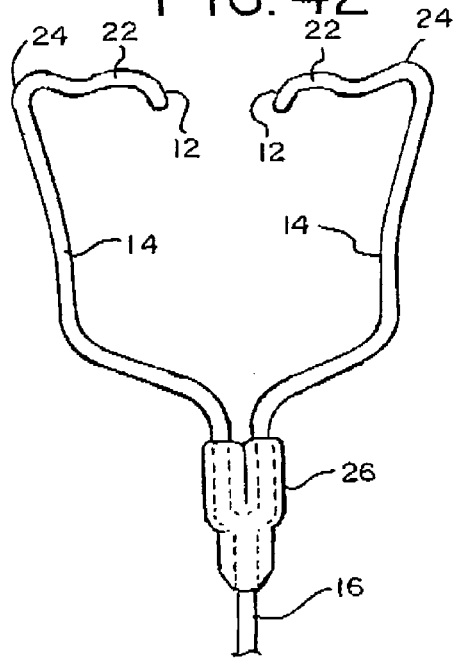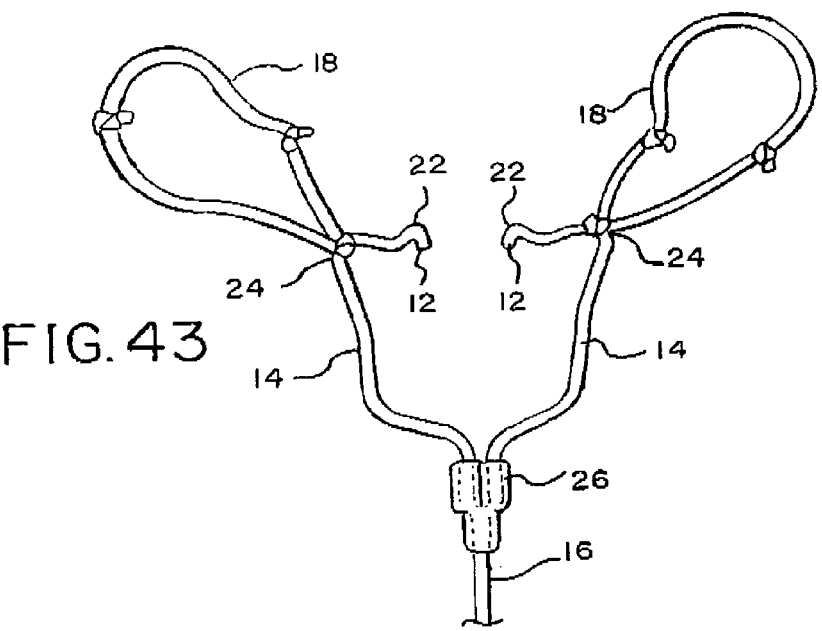

ORAL MOUTHPIECE AND METHOD FOR THE USE THEREOF

This application is a continuation of U.S. application Ser. No. 13/954,314, filed Jul. 30, 2013, which is a continuation of U.S. application Ser. No. 13/040,058, filed Mar. 3, 2011, which application claims the benefit of U.S. Provisional Application No. 61/310,590, filed Mar. 4, 2010 and entitled Portable High Frequency Air Pulse Delivery Device, U.S. Provisional Application No. 61/311,145, filed Mar. 5, 2010 and entitled Oral Mouthpiece and Method for Use Thereof, and U.S. Provisional Application No. 61/417,041, filed Nov. 24, 2010 and entitled Oral Mouthpiece and Method for the Use Thereof, the entire disclosures of which are hereby incorporated herein by reference.

FIELD OF THE INVENTION

This invention relates to oral appliances and in particular a mouthpiece used to deliver at least one substance or stimulus.

BACKGROUND OF THE INVENTION

Swallowing is a complex behavior in which the output of an integrative brainstem network gives rise to a patterned movement sequence described as the pharyngeal stage of swallowing. While several lines of evidence have demonstrated the importance of oropharyngeal sensory inputs in activating this medullary swallowing network, the range of afferent patterns that are both necessary and sufficient to evoke swallowing has not been fully elucidated. Stimulation of receptive fields innervated by the superior laryngeal nerve (SLN) or the pharyngeal branch of the glossopharyngeal nerve (GPNph) appear to be particularly effective in evoking or modulating the pharyngeal swallow; these "reflexogenic" areas correspond to the laryngeal mucosa, including the epiglottis and arytenoids, the lateral pharyngeal wall, posterior tonsillar pillar and peritonsillar areas.

In humans, the anterior faucial pillar historically has been considered the most reflexogenic site for swallowing. However, the recent finding that the pharyngeal swallow may begin after the bolus head passes the anterior faucial pillars in healthy adults, including geriatric adults, suggests that stimulation of more posterior pharyngeal regions may help facilitate the initiation of swallowing. The importance of more posterior oropharyngeal areas in swallowing elicitation is also suggested by anatomic evidence that the human posterior tonsillar pillar, as well as discrete regions of the palate, pharynx and epiglottis are innervated by a dense plexus formed from the GPNph and the internal branch of the SLN. The spatial correspondence between these areas of dual SLN/GPNph innervation and reflexogenic areas for swallowing has lead to the hypothesis that swallowing is elicited most readily by stimulation of areas innervated by both the GPNph and SLN. Dynamic stimuli that excite primary afferents within a number of receptive fields over time appear to elicit swallowing more readily than do static stimuli.

A variety of stimulus modalities have been applied in attempts to evoke swallowing (for review, see Miller, 1999). Repetitive electrical stimulation of the SLN or the GPN, particularly at stimulation frequencies between 30 and 50 Hz, evokes swallowing in a number of animal species. This suggests that the repetitive nature of the stimulus, and the repetition rate, are critical variables in swallowing elicitation. More recently, electrical stimulation of the pharynx has been reported to increase both the excitability and size of the pharyngeal motor cortex representation in humans (14), and facilitate swallowing in dysphagic patients following stroke. Mechanical and chemical stimuli can evoke swallowing in animal species. In humans, reports of the effects of cold mechanical stimulation of the anterior tonsillar pillar have been variable, some authors reporting decreases in swallowing latency and increases in swallowing frequency (16), and others failing to find an effect of this type of stimulation on oropharyngeal bolus transit, esophageal coordination, or the temporal pattern of swallowing. Three studies have examined the effects of cold mechanical stimulation applied to the anterior tonsillar pillars in small samples of dysphagic stroke patients. They reported a short-term facilitation of swallowing, measured in terms of reduced delay of the pharyngeal swallow, in some patients, with no related reduction in aspiration. Longitudinal studies, examining the potential long-term effects of oropharyngeal sensitisation on not only swallowing physiology but also on nutritional and respiratory health, have not been reported. Reports on the effects of gustatory stimuli also have been variable. A sour bolus has been reported to facilitate swallowing in stroke. Whereas some authors have reported that swallowing latency is significantly reduced by a combination of mechanical, cold, and gustatory (sour) stimulation, others have reported that a cold plus sour bolus reduces the speed of swallowing.

Air-pulse trains also have been considered as a stimulus that may facilitate the pharyngeal swallow. For example, a single air pulse is a dynamic stimulus that could be applied to a number of receptive fields including regions innervated by both the GPNph and SLN. Furthermore, an air-pulse train represents a repetitive stimulus that can be applied at specific frequencies and pressures. Some devices have been suggested for delivering such air-pulse trains, as disclosed for example in US patent application 2010/0016908, the entire disclosure of which is hereby incorporated herein by reference. The air pulse trains are directed to the oral cavity by way of an oral device, which is positioned and secured through various devices. For example, the '908 publication describes, in one embodiment, an "over-the-ear" oral device configured such that the flexible tubing that delivers the air pulse trains wraps around the ears of the user.

SUMMARY

The present invention is defined by the following claims, and nothing in this section should be considered to be a limitation on those claims.

In one aspect, an oral device, or mouthpiece, is provided for delivering a stimulus, for example and without limitation a fluid, to the mouth or oropharynx of a user. In one embodiment, the oral device includes three portions: an intraoral portion, an extraoral portion, and an auxiliary support device. The auxiliary support device may include two ear loops (i.e., located on the right and left sides of the mouthpiece), or a band that surrounds the user's head, and which serve to stabilize the oral device. In one embodiment, the ear loops are knitted elastic. The intraoral portion generally includes at least one outlet port through which at least one agent or stimulus is delivered to the oral cavity or oropharynx. In one embodiment, the extraoral portion generally includes at least one (proximal) inlet port (or connector) that is connected to a control system (i.e., that generates the "agent(s)"), and at least one distal end that is continuous with the intraoral portion of the oral device.

In other embodiments, the auxiliary support device may include one or more support frames or members, including without limitation a Y-shaped yoke, a U-shaped frame, or a laterally extending support member that engages the user's face above or at an upper lip.

In other embodiments, an oral mouthpiece includes a pair of laterally spaced intraoral portions defining intraoral conduits each having at least one outlet port adapted to dispense at least one fluid pulse and an extraoral portion integrally formed with each of the intraoral portions. The extraoral portions include a pair of spaced apart lip bends communicating with the intraoral portions and a pair of chin portions extending downwardly from the lip bends, with the chin portions forming a loop positionable under the user's chin. The oral mouthpiece may be deployed with or without an auxiliary support device.

In another aspect, a method of delivering a fluid to a predetermined location in a user's mouth includes disposing a flexible tube between an outer side of a row of teeth and an inner surface of a cheek, securing the flexible tube to the user with an auxiliary support device separate from the tube and formed from a different material than the flexible tube, and dispensing the fluid through the exit port.

The various oral devices and methods for the user thereof provide various advantages. For example and without limitation, the oral device may be easily and securely positioned on the user in a reliable manner without impinging on the face of the user, and without interfering with other accessories, such as eyeglasses or hearing aids, positioned on the user.

The foregoing paragraphs have been provided by way of general introduction, and are not intended to limit the scope of the following claims. The various preferred embodiments, together with further advantages, will be best understood by reference to the following detailed description taken in conjunction with the accompanying drawings.

BRIEF DESCRIPTION OF THE DRAWINGS

The invention will now be described by way of example only, with reference to the accompanying drawings, in which:

FIG. 1 is a plan view of the oral mouthpiece of the present invention;

FIG. 2 is front view of a user with the oral mouthpiece of FIG. 1 located in an operational position;

FIG. 3 is a plan view of an alternate embodiment of the oral mouthpiece of the present invention;

FIG. 4 is a front view of a user with the oral mouthpiece of FIG. 3 located in an operational position;

FIG. 5 is a side view of the user of FIG. 4;

FIG. 6 is a plan view of an alternate embodiment of the oral mouthpiece of the present invention similar to that shown in FIG. 1 but showing a plurality of ports;

FIG. 29 is a perspective view of an alternative embodiment of a yoke.

FIG. 30 is a partial end view of one side of the yoke shown in FIG. 29.

FIG. 31 is a perspective view of an alternative embodiment oral device.

FIG. 39 is a front view of the oral mouthpiece shown in FIG. 1 as applied to a user.

FIG. 40 is a side view of the oral mouthpiece shown in FIG. 29 as applied to a user.

FIG. 41 is a side view of the oral mouthpiece shown in FIG. 1 without an auxiliary support device secured thereto.

FIG. 42 is a front view of the oral mouthpiece shown in FIG. 41.

FIG. 43 is a front view of the oral mouthpiece shown in FIG. 42 with an auxiliary support device secured thereto.

DETAILED DESCRIPTION OF THE DRAWINGS

Figure 7:
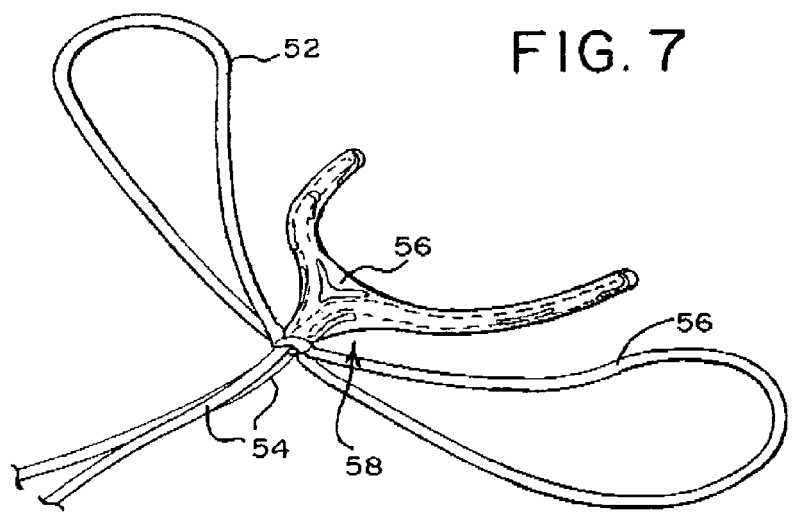
FIG. 7 is a perspective view of another embodiment of the oral mouthpiece of the present invention.

Referring to FIGS. 1, 2 and 39-43, one embodiment of an oral mouthpiece is shown generally at 10. The oral mouthpiece 10 includes intraoral portions 12, extraoral portions 14 and an auxiliary support device, configured in this embodiment as ear connectors 18. The extraoral portions 14 include a supply portion 16. The intraoral portions 12 define intraoral conduits. The extraoral portions 14 define an extraoral conduit. The intraoral conduit is in flow communication with the extraoral conduit.

The intraoral portion 12 of the mouthpiece 10 enters the mouth at the angle or corner of the mouth on the user's right and left sides. The intraoral portion 12 extends along the buccal cavity, or vestibule, lateral to the teeth and medial to the cheek, on the right and left sides of the mouth. The length of the intraoral aspect is typically between 20 mm and 50 mm for human adult users, and may be less for pediatric users. The lengths of the intraoral portions may be modified by the user by advancing, or retracting, the intraoral segment that is in flow communication with the extraoral segment, relative to the auxiliary support device. This is an advantage of the device in that the intraoral segments may be modified to accommodate the user's specific oral anatomy. The intraoral portion or aspect 12 ends caudally with an output port 20 such that an agent or substance or stimulus can be delivered from this output port 20 in the general region of the posterior mouth or oropharynx on the right and left sides.

In one embodiment, the intraoral portion 12 is oriented superiorly and caudally within the buccal cavity such that the output port 20 is situated lateral to the maxillary premolars or molars during use. One advantage of having the intraoral portion or aspect 12 angled superiorly from its origin at the corner of the mouth is that the output port 20 of the mouthpiece does not come in contact with pooled saliva that may accumulate in the region of the mandibular dental arch. However, the intraoral portion 12 of the mouthpiece may be oriented along a variety of angles, relative to the horizontal plane, providing a means for positioning the output port 20 lateral to the mandibular molars, or along the occlusal plane, depending upon the specific conditions and requirements of the user including the oral anatomy and the dentition.

In another aspect, the intraoral portion 12 of the mouthpiece 10 may be oriented along a variety of angles, relative to the user's sagittal plane, and be gently curved, along this principal off-sagittal orientation, such that it follows the natural contour of the buccal cavity and maxillary or mandibular dental arches, thereby providing optimal comfort for the user. The general orientation and local curvature of the intraoral portion 12 can be provided as manufactured aspects of the mouthpiece 10. Alternatively, the mouthpiece can be provided such that these aspects of the intraoral portion 12 can be manually molded by the clinician, caregiver, or user. The capacity to orient and curve the intraoral aspect of the mouthpiece can be provided by a length of fine malleable wire being embedded within the intraoral portion 12 of the mouthpiece on the left and right sides of the mouth. This may represent an advantage in that the user, or caregiver, would be provided a means of molding the mouthpiece to the specific anatomy of the individual user.

In another aspect, the intraoral 12 and extraoral 14 portions of the mouthpiece are continuous as right and left or pair of first looped regions 22 of mouthpiece that are positioned at the right and left angles or corners of the user's mouth during use. These two looped regions, which form lip bends, are oriented approximately in parallel with the user's axial or horizontal plane, at the level of the angles of the mouth.

The looped regions 22 where the intraoral 12 and extraoral 14 portions of the mouthpiece meet at the angles of the mouth are contiguous with a second, extraoral looped or curved region 24 that provides a site of attachment or site of origin for an auxiliary support device. In other embodiments, the looped region 24 may be omitted. In one embodiment, the auxiliary support device is configured as ear connectors 18 that are attached on the right and left sides of the mouthpiece 10. The ear connectors 18 may be ear loops that are made of a different material than the intraoral or extraoral portions. In one embodiment, the ear loops are knitted elastic ear loops. The second looped region 24 is oriented at approximately 45 degrees relative to the sagittal plane of the user on the right and left sides of the mouthpiece. In use the second looped regions 24 sit over the face, immediately lateral to the angle of the mouth on the right and left sides, and does not extend rearwardly and/or upwardly for connection to the ears of the user. Rather, these looped regions 24 provide a point of origin for the auxiliary support device, such as the around-the-ear soft elastic ear loops 18 on the right and left sides of the mouthpiece. By virtue of their orientation relative to the intraoral portions, these ear loop origin sites and associated ear loops provide a means of stabilizing the intraoral segments 12, without the elastic tending to pull the intraoral segment 12 out of the mouth. These looped regions 22 and 24 are continuous with a communicating region that extends inferiorly from the inferior aspect of the second looped portion for approximately 30 mm to 100 mm and then curves medially toward the user's midline plane so as to form a chin loop. As the right and left portions of the mouthpiece approach the midline, they articulate with a Y-connector 26, providing a means of delivering an agent from a single input post to right and left intraoral aspects of the mouthpiece.

Figure 44:
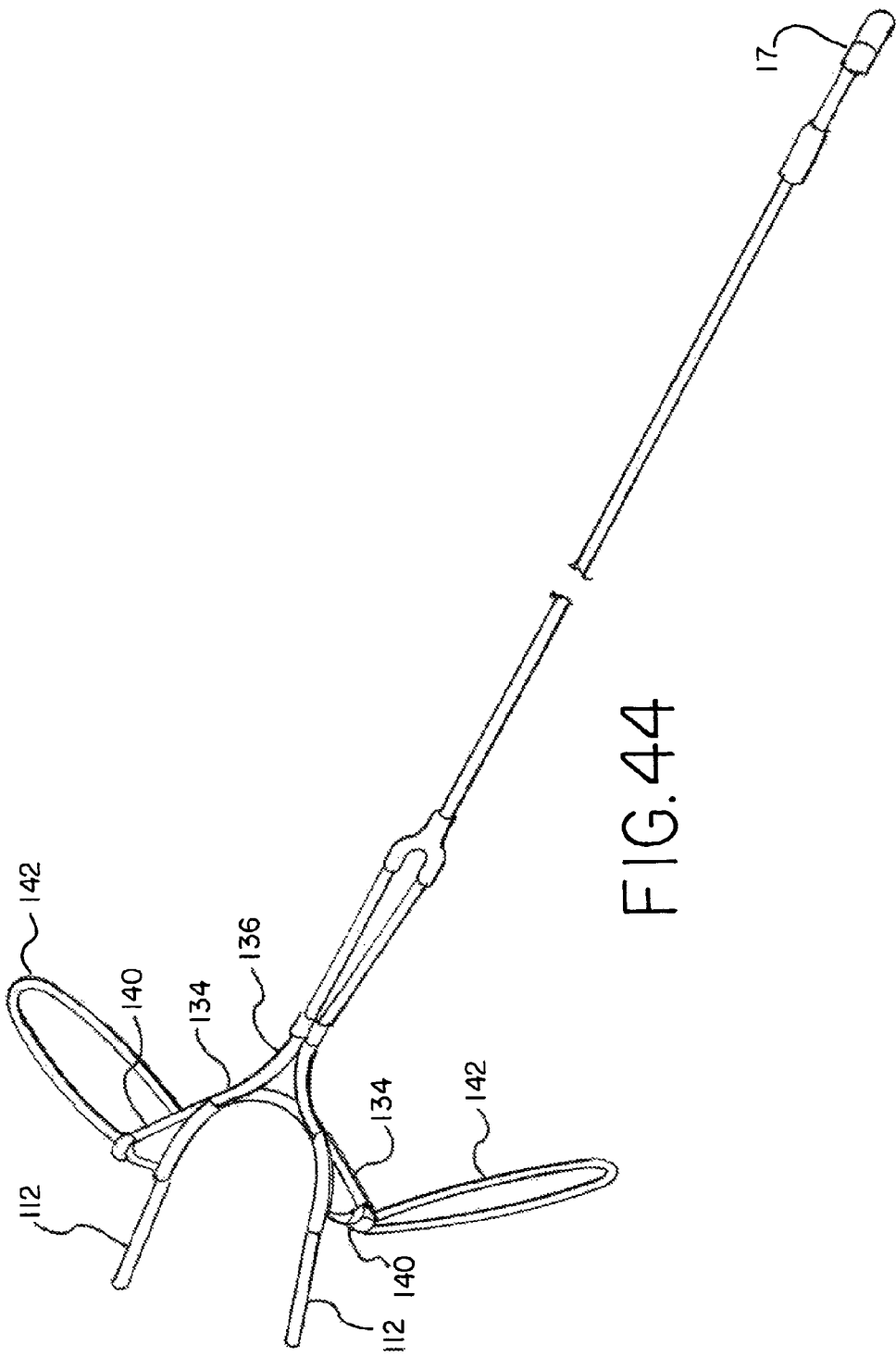
FIG. 44 is a perspective view of one embodiment of an oral mouthpiece.

In one embodiment, the Y-connector 26 is connected to the supply portion 16 of the mouthpiece 10, which supply portion continues for approximately 90 cm. The length of the supply portion 16 may extend from 0.50 meters to about 2.0 meters as shown in FIG. 44. A longer supply portion 16 is an advantage in that the mouthpiece user may move fairly freely in relation to the fluid control unit. For example, the mouthpiece use could move between lying and sitting in a hospital bed with the fluid control unit mounted on the head or side rail of the bed. This feature increases the clinical utility of the mouthpiece system in the health care and home settings. At the end of the supply portion tube, a male luer connector may be provided. Alternatively, a low pressure one-way check valve luer connector 17 is provided. This is to prevent contamination of the control unit by any fluids, bodily or otherwise, that may traverse the tubing 16. The check valve 17 may reduce the flow into the mouthpiece, dropping the flow rate to 2.4 to 2.5 L/min. The flow may be maintained above 2.0 L/min. The frequency and amplitude are not affected by the inclusion of the check valve 17.

A control unit 28 is connected to the distal end of the supply portion 16 of the mouthpiece 10. The control unit 28 generates at least one agent, or delivers at least one agent to the supply portion 16 of the mouthpiece 10. Preferably the Y-connector is adjustable so that it can extend past the cheek/jaw thereby minimizing a patient's tendency to dislodge the mouthpiece. However, there may be instances when a longer portion 14 is desirable, for example, in patients who are very sensitive to contact about the face and mouth.

Figure 32:
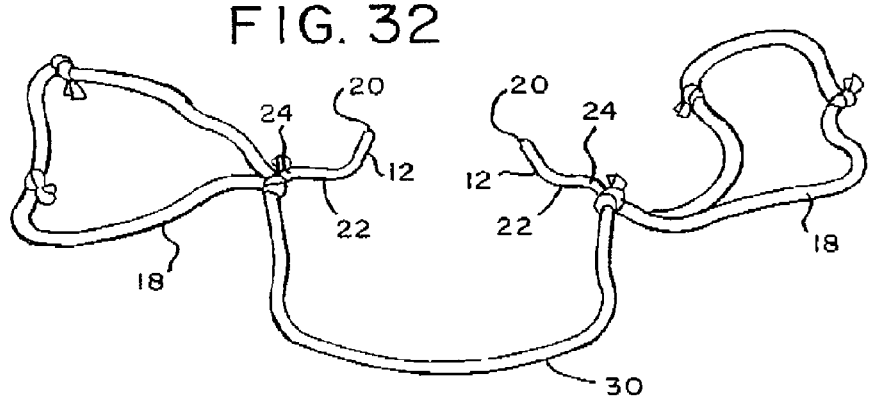
FIG. 32 is a front, perspective view of the oral mouthpiece shown in FIG. 3.
Figure 33:
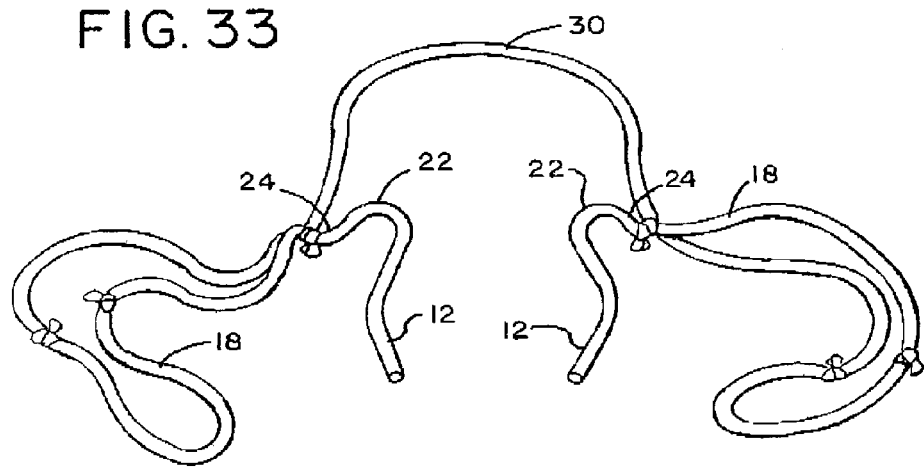
FIG. 33 is a top view o the oral mouthpiece shown in FIG. 32.
Figure 34:
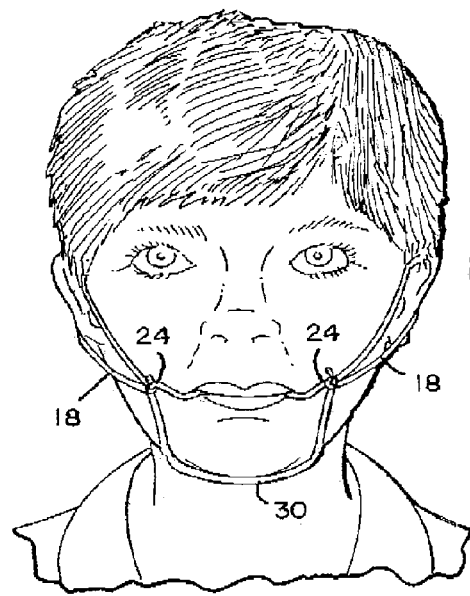
FIG. 34 is a front view of the oral mouthpiece shown in FIG. 32 applied to a user.
Figure 35:
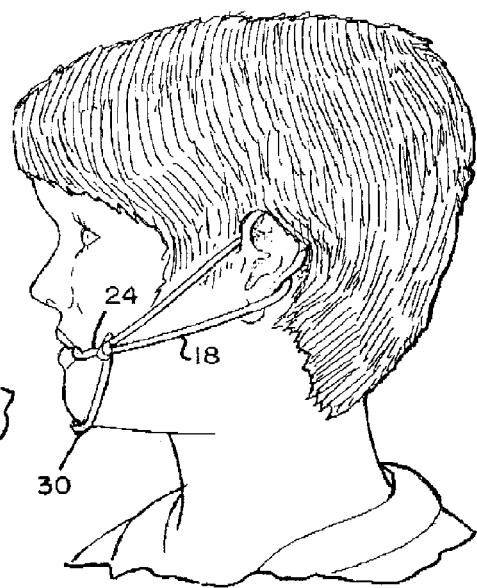
FIG. 35 is a side view of the oral mouthpiece shown in FIG. 32 applied to a user.
Figure 36:
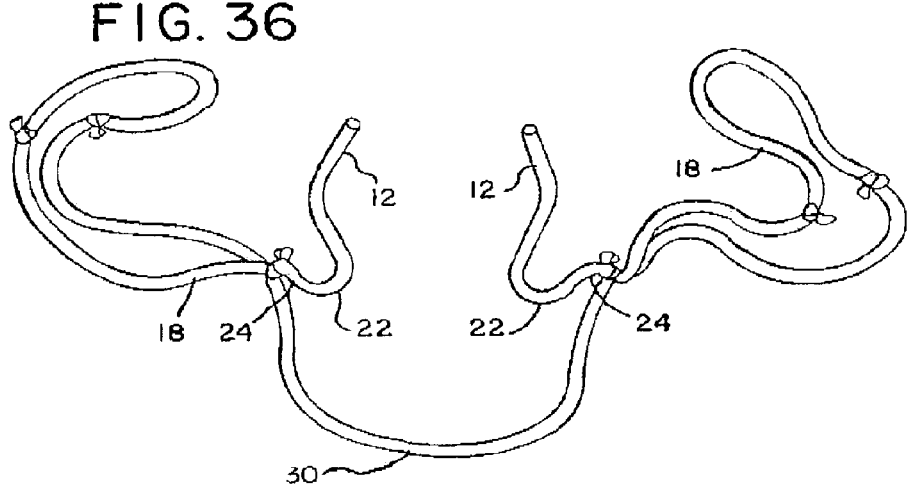
FIG. 36 is an alternative to view of the oral mouthpiece shown in FIG. 33.

In another embodiment shown in FIGS. 3-5 and 32-36, a continuous chin loop or region 30 is provided, extending from the right elastic attachment loop 24 (shown in FIGS. 3 to 5) and, running inferiorly to the level of the user's chin, crossing the midline immediately anterior to the chin, and extending to the other side of the face where it runs superiorly and continues as the left elastic attachment loop 24 as best seen in FIGS. 4 and 32.

In another aspect, one embodiment of the auxiliary support device is configured as ear loops 18 attached to the second looped 24 aspect of the extraoral portion 14 of the mouthpiece 10, described above. In one embodiment, the ear loops 18 are made of knitted nylon polyester elastic and are between 4 cm and 25 cm in length and between 1 mm and 7 mm in width. The ear loops 18 originate from a single site on the second curved portion 24 of the mouthpiece 10. There are several advantages afforded by the ear loops 24. In one embodiment, the auxiliary support device, and in particular the ear loops or head band, are more compliant or flexible (less stiff) than the extraoral and/or intraoral portions. For example, the ear loops or head band may have a much lower modulus of elasticity than the intraoral and extraoral portions, made for example of thermoformed tubing. The ear loops or head band provide a means of stablilizing the mouthpiece during use. Being made of soft, knitted elastic material such as nylon polyester, the ear loops stretch substantially such that the mouthpiece can be effectively and comfortably stabilized and worn by individuals with different cranial and facial anatomy. The soft knitted material reduces the likelihood that the mouthpiece will cause discomfort or tissue damage to the hairy skin of the face or pinna. The narrow width and malleability/flexibility of the knitted elastic ear loops is another advantage in that the ear loops do not interfere with over-the-ear hearing aids or the over-the-ear portion of eyeglasses. This is particularly important since users of the mouthpiece will include older adults, as well as pediatric users who require eyeglasses and hearing aids as the result of congenital syndromes or conditions. The soft, knitted ear loops provide user comfort, even when the mouthpiece is used for extended periods of time.

In use, some flexibility at points 20, 22, and 24 provide a means of improving the fit, efficacy, and comfort of the mouthpiece for faces of various shapes and sizes. Some degree of malleability in the chin piece 30 (shown in FIGS. 3 to 5) and extraoral portions 14 (shown in FIGS. 1 and 2) is also advantageous in that this allows improved positioning of the two sections that rise up toward the angles of the mouth.

Another advantage of the knitted ear loops 18 is that many users, caregivers, and clinicians are familiar with them based on previous experience with ear loops on medical masks. Thus, the ear loops 18 will facilitate easy positioning of the mouthpiece by users by virtue of their general familiarity with the procedures around knitted ear loops. Even for users who have not previously used knitted ear loops, there is an intuitive element around ear loops that would increase the likelihood that a naive user would position them correctly around the ears.

The mouthpiece 10 may be made of flexible tubing, for example, a pair of flexible tubes configured to be positioned on opposite sides of the face of a user. The oral device may include only a single tube positioned on one side of the user's face, for example, for the purpose of delivering an agent to one side of the mouth or oropharynx. This may be advantageous, for example, in patients who have undergone unilateral surgery for oral cancer, or in the case of a unilateral sensorimotor impairment of the face, mouth, or oropharynx.

The flexible tubes may be made of tubing which can be shaped into a given configuration but which has some flexibility and ability to conform to the face and mouth of the user. The tubes may have a ⅛th inch outer diameter and a ¹⁄₁₆th inner diameter forming a lumen. In various embodiments, the intraoral and/or extraoral portions may be made of various materials, including without limitation, polyurethane, polyethylene, PVC, silicone, rubber, or other suitable and biocompatible materials, and/or combinations thereof. In one embodiment, the tubing is 1.6 mm ID×3.2 mm OD tubing made of TYGON® MPF-100 available from Saint-Gobain, Akron, Ohio.

It will be appreciated by those skilled in the art that the intraoral portions 12 may have a plurality of ports 40 formed therein in addition to the ports 20 positioned at the distal end of the intraoral portions 12.

Figure 37:
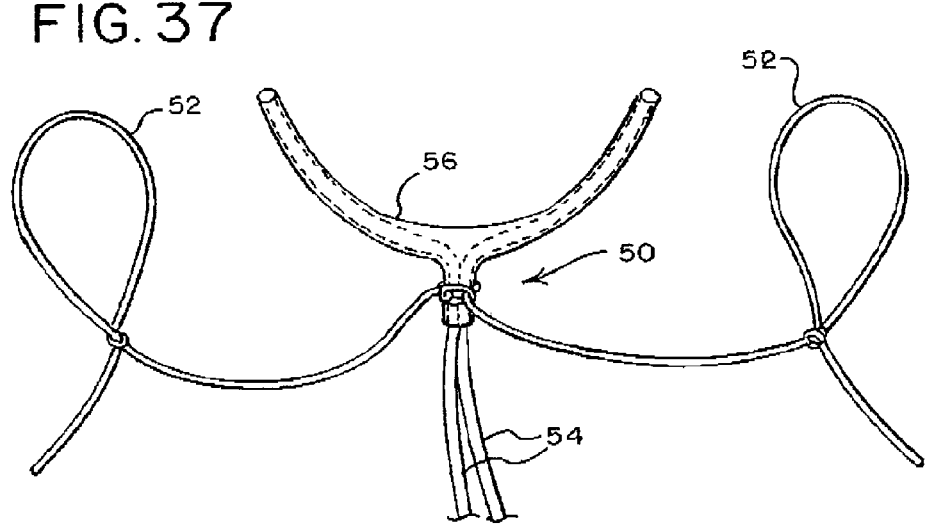
FIG. 37 is a top view of the oral mouthpiece shown in FIG. 7.
Figure 38:
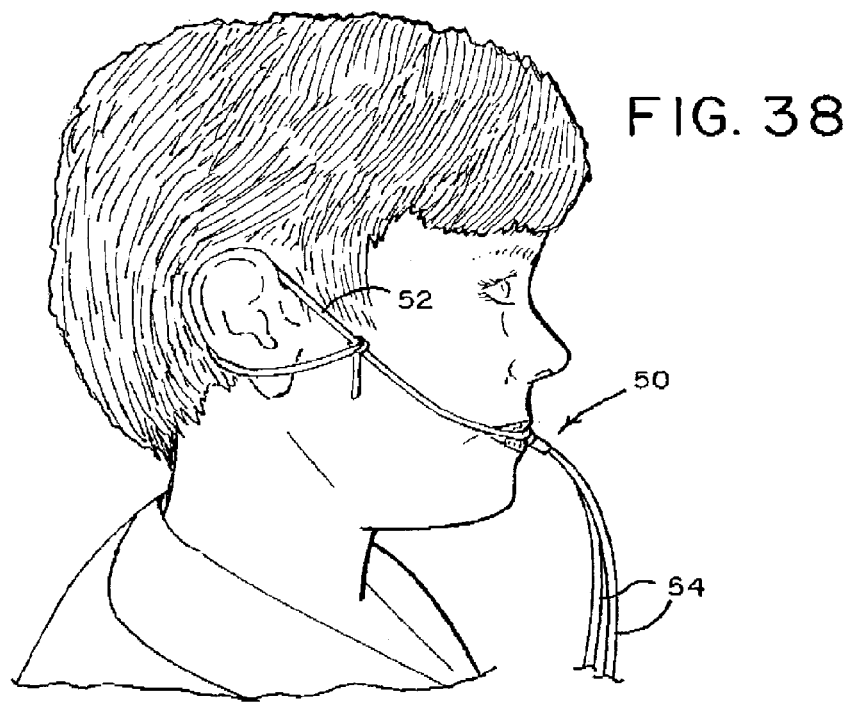
FIG. 38 is a side view of the oral mouthpiece shown in FIG. 37 as applied to as user.

Referring to FIGS. 7, 37 and 38, the oral device 50 shown herein and fully described in US 2010/0016908 and WO 2009/127947, both of which are hereby incorporated herein by reference, may be improved upon by adding an auxiliary support device, shown as ear loops 52. Ear loops 52 are similar to those described above but are attached to the extraoral portion 54 proximate to where the extraoral portion 54 meets the intraoral portion 56. While the ear loops 52 serve to secure the oral device 50 to a user in a secure fashion. In the absence of earloops, this embodiment has the shortcoming that it can move out of position when the subject opens his/her mouth, or in patients with mouth/lip weakness the mouthpiece 50 could move out of position during use.

Figure 23:
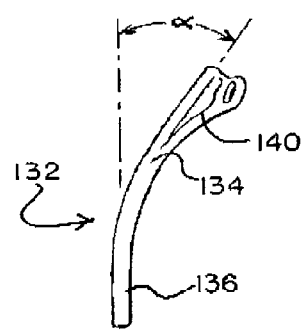
FIG. 23 is a side view of the yoke shown in FIG. 20.
Figure 21:
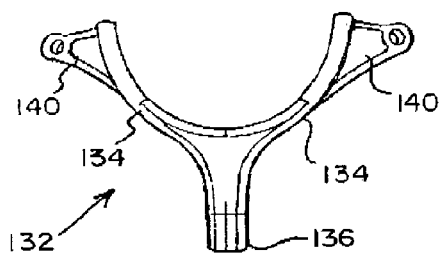
FIG. 21 is a front view of the yoke shown in FIG. 20.
Figure 22:
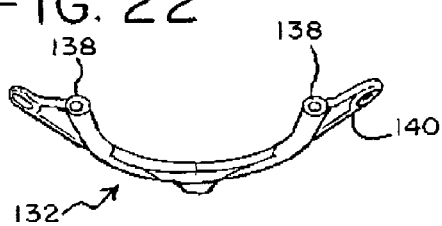
FIG. 22 is a top, perspective of the yoke shown in FIG. 20.
Figure 20:
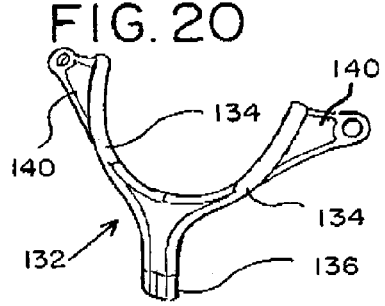
FIG. 20 is a perspective view of the yoke shown in FIG. 19.

Referring to FIGS. 19-23, 29-30 and 44, another embodiment of an oral device is shown. The oral device includes a pair of laterally spaced intraoral portions 112 defining intraoral conduits each having at least one outlet port 120 adapted to dispense at least one fluid pulse. An extraoral portion 114 is integrally formed with each of the intraoral portions. The extraoral portions define extraoral conduits in flow communication with the intraoral conduits. An auxiliary support device includes a yoke. In one embodiment, the yoke is configured as a Y-shaped frame 132 having a pair of arm portions 134 and an inlet portion 136, each configured with grooves or channels in which the extraoral portions are disposed and secured. As shown in FIG. 23, the arm portions curve rearwardly from the inlet portion. In one embodiment, the arm portions extend at an angle α of about 20-60 degrees, and in one embodiment at an angle α of about 30-45 degrees, and in one embodiment at an angle α of 38.5 degrees. The frame shapes and holds the extraoral portions. In addition, each of the pair of arm portions 134 includes a wing with an attachment member 140. At least one securing member 142, configured for example and without limitation as an elastic band, may be secured to the attachment members 140. The band may be configured as a pair of ear loops, or as a single headband that encircles the user's head and locates and holds the yoke in position.

Referring to FIGS. 29 and 30, in one embodiment, wing portions 440 have a concave curved portion 444 that interfaces with the lips, or corner of the user's mouth, with the end portions 442 of the yoke arms extending into, and positioning intraoral portions of the tubing, in the mouth of the user. In essence, the end portions 442 and the attachment member 140 have a recess 446 formed therebetween so as to locate the yoke relative to the user, and the lips/mouth in particular, with the force applied by the securing member 18 urging the yoke against the user's lips/mouth. Referring to FIG. 30, the width (W) of the wing 440 may be widened at the junction 448 of the end portions 442 and the wings 440 at the area of contact with the user's lips/mouth so as to reduce the tissue contact pressure.

Figure 24:
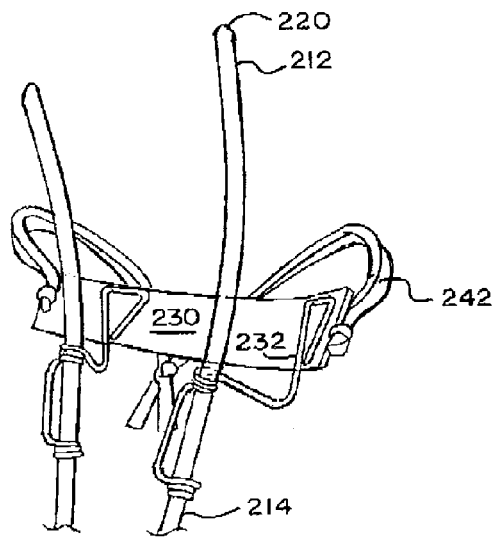
FIG. 24 is a partial, perspective view of an alternative embodiment oral device.
Figure 25:
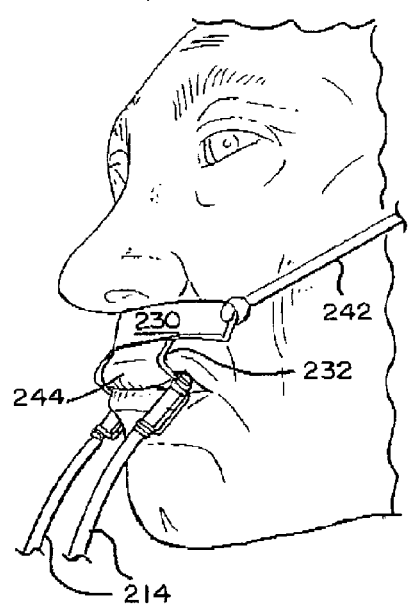
FIG. 25 is a side view of the oral device shown in FIG. 24 applied to a user.
Figure 26:
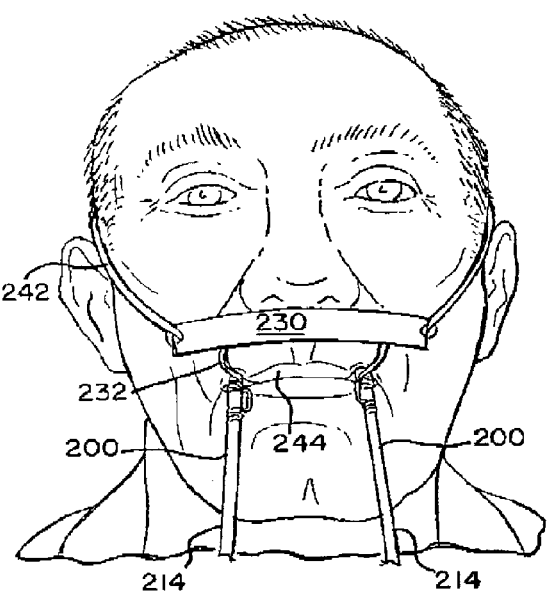
FIG. 26 is a front view of the oral device shown in FIG. 24 applied to a user.

Referring to FIGS. 24-26, another embodiment of the oral device includes a pair of tubes 200, each defining intraoral and extraoral portions, and which may be configured as substantially straight, flexible tubes, or may include lip bends as described above. A laterally extending support member 230 extends transversely to the tubes 200 and is positioned above an extraoral portion 214. The support member 230 may engage the user's face above or on/at an upper lip thereof. The support member 230 may be made of a cloth-like material, and may be elastic or non-elastic. The support member is coupled to the tubes 200 with a pair of clips 232. The clips 232 may be wrapped around the tubes, and are secured to the support member with fasteners, adhesives or combinations thereof. The clips 232 may include a lip bend portion that wraps around the upper lip of the user. At least one securing member 242 is coupled to opposite ends of the support member. The securing member may be configured as a pair of ear loops, or as a single head band. In use, the intraoral portions 212 are disposed in the user's mouth, with the support member 230 supported by the user's upper lip and securely held thereto with the securing member 242. This device may be particularly well suited for individuals that may have particular ailments or sensitivities around and under the chin.

Figure 27:
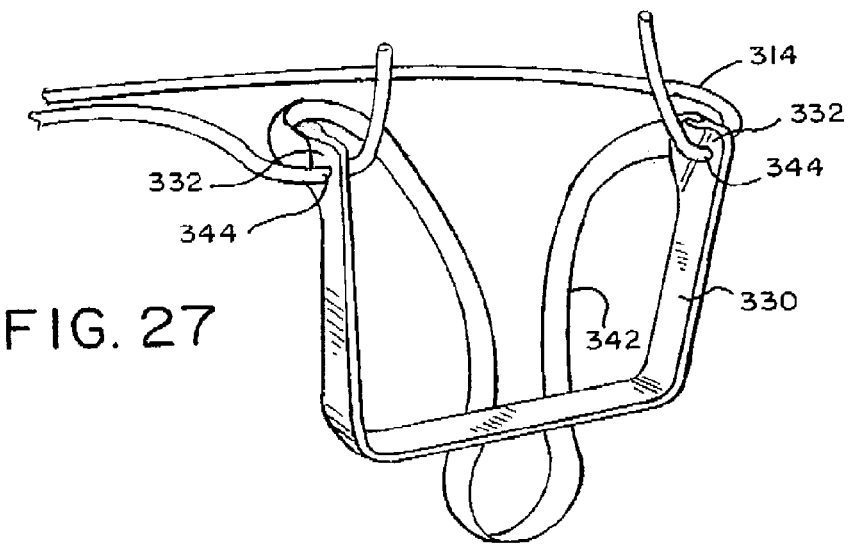
FIG. 27 is a partial, perspective view of an alternative embodiment oral device.
Figure 28:
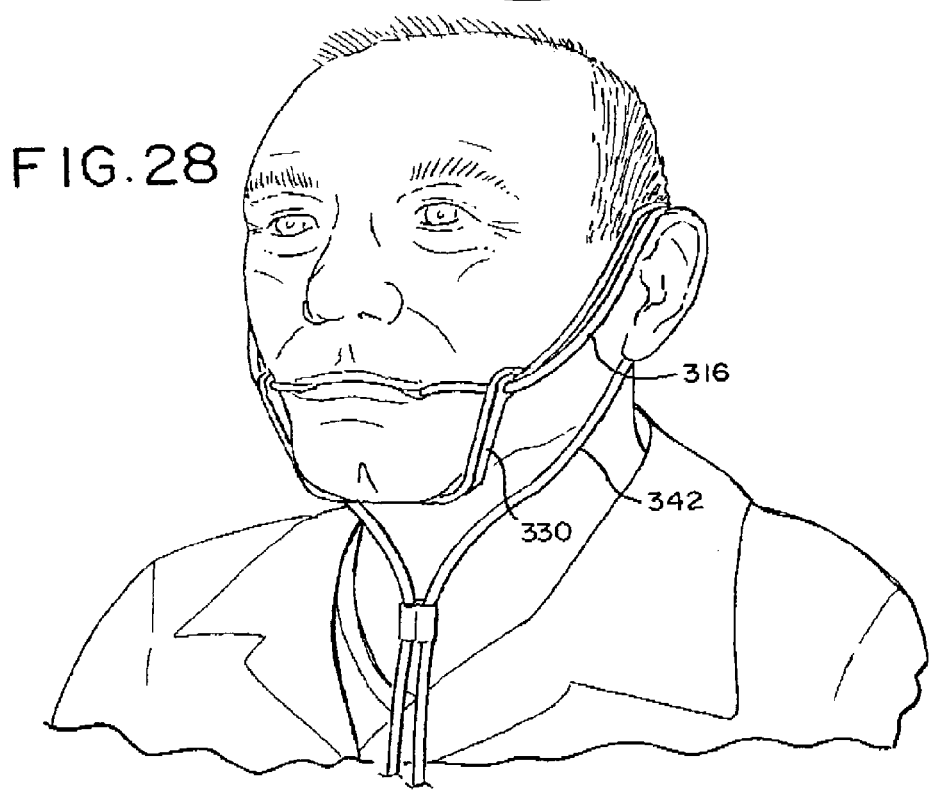
FIG. 28 is a perspective view of the oral device shown in FIG. 27 applied to a user.

Referring to FIGS. 27 and 28, another embodiment of an auxiliary support device includes a U-shaped frame 330 shaped and configured to be positioned under the user's chin. The frame has opposite end portions 332 coupled to an extraoral portion 314, and at least one securing member 342 coupled to the opposite end portions 332. For example, the tubes making up the extraoral portions may extend through openings 344 formed in the end portions. The U-shaped frame may be made from a flexible, but semi-rigid material, such as a plastic strip. The extraoral portions 314 may include ear loop portions 316, thereby forming an integral securing member, or may extend downwardly along the chin as shown for example in the embodiment of FIG. 1. At least one securing member 342, configured as individual ear loops or as a head band may be additionally secured to the end portions, or may be the sole support for the end portions. The securing member locates and holds the support device firmly in position.

Referring to FIG. 31, another embodiment of an oral device 500 includes a pair of downwardly extending extraoral inlet portions 502, each configured with an attachment member 504, or loop, that may be coupled to a securing member, such as an ear loop or head band. The inlet portions have an opening 508 shaped and dimensioned to receive an auxiliary extraoral tube 506. The oral device further includes integrally formed intraoral portions 510, which are shaped and contoured to be positioned in the vestibule of the user's mouth between the teeth and inner cheek/lips. The intraoral portions are in fluid communication with the extraoral inlet portions, and thereby with the tubes 506 positioned in the inlet portions. The ends of the intraoral portions are each configured with a fluid exit port 512. An intraoral bridge 514 extends between the opposing pairs of inlet portions/intraoral portions. The bridge 514 is curved and shaped/dimensioned to be positioned in the vestibule. A cutout 516, or clearance opening, is formed in a mid/intermediate portion of the bridge to provide clearance for the maxillary labial frenulum. In one embodiment, the intraoral portions and bridge 510, 514 are positioned between the upper teeth and the user's cheek, with the inlet portions 502 extending downwardly. In another embodiment, the intraoral portions are positioned between the lower teeth and cheeks, with the inlet portions extending upwardly. A securing member 18, e.g., ear loops or head band, is coupled to the attachment members and secures the oral device to the user. The oral device may be made of a molded rubber compound, or of various polymers otherwise herein described.

In any of the embodiments, a wire may run along a length of at least a portion of the flexible tubing forming either or both of the intraoral and extraoral portions. The wire provides further shape memory to the flexible tubing. For example, the oral devices disclosed herein may be shaped by inserting a length of fine wire into the tubing and then bending the wire.

There are a number of advantages realized with the different embodiments of the oral mouthpiece of the present invention. Specifically the mouthpiece is stabilized during use by the user by the auxiliary support devices, including for example and without limitation the soft elastic loops that fit around the ears. This advantage provides a means of maintaining the intraoral aspects of the mouthpiece in appropriate position, even when the lips are open (as in the case of a patient with lip weakness), during talking, and during other behaviours such as yawning, eating, chewing, and drinking from a glass or straw. Importantly, this feature of the mouthpiece prevents the intraoral portions of the mouthpiece from migrating toward the pharynx, or in other directions, during use by a person, thus enhancing the safety aspect of the device.

Use of the auxiliary support devices stabilizes the mouthpiece so as to reduce the likelihood that the stabilization component of the mouthpiece will be perceived as irritating by the user and cause tissue damage with prolonged use.

The head band and soft, elastic ear loops are intuitive in terms of positioning, since they are used in other devices with which the user has likely had previous experience, for example, a medical face mask. The head band and soft elastic ear loops are straightforward to manipulate, thereby facilitating correct positioning by patients. The elastic bands are also narrow, occupying very little area over and around the pinna of the ear or rear of the skull, thus allowing easy positioning and use by persons who wear glasses or over-the-ear hearing aids.

In the various embodiments, there is no mouthpiece material occupying the midline region of the mouth. Rather, the intraoral portions of the mouthpiece enter the mouth as the angles of the mouth on the left and right sides, leaving the midline oral region free to engage in talking, eating, drinking, and other oral behaviours, and providing a situation in which the appearance of the mouthpiece is considered more socially appropriate than with devices that occupy the midline oral region. Of course, it should be understood that the conduit may extend along the midline of the chin, and then diverge to the left and right sides of the mouth.

The tubing comprising the mouthpiece is molded such that the left and right intraoral portions extend outside the mouth at the angles as an extraoral portion that is continuous between the right and left sides, and that extends inferiorly to run laterally at the level of the chin. An important advantage of this aspect of the mouthpiece is that it prevents the mouthpiece from being swallowed. In one embodiment, this extraoral portion of the mouthpiece can be used to further tether the mouthpiece, or to attach other devices.

The mouthpiece is relatively small and light-weight. In one preferred embodiment, it is envisaged that the mouthpiece can be readily manufactured at minimal cost, given the simplicity of the design, the small length of tubing required, and the low costs of the other required materials such as the elastic.

The mouthpiece can be easily connected to the output of an air-pressure regulator through a length of tubing that extends from the extraoral portion of the mouthpiece in the region of the mandible.

The mouthpiece comes manufactured with a looped configuration, oriented on the horizontal plane that fits around the angle of the mouth. This aspect of the tubing is contiguous with a second loop that is situated extraorally, immediately lateral to the angle of the mouth and oriented approximately 45 degrees relative to the user's midsagittal plane. The soft elastic ear loops originate at this second looped region and extend over and around the pinna of the ears. With this design, the elastic ear loops do not pull directly on the intraoral portions of the mouthpiece, causing them to migrate. Rather, the elastic ear loops pull on the second looped area (described above) with the result that the intraoral portions of the mouthpiece remain stable during use.

The mouthpiece can provide an attachment platform for other oral device(s), or oral device components.

The mouthpiece can be used as an oral suction catheter.

The intraoral portions of the mouthpiece can be provided as colored elements, providing a cue to the user regarding the portion of the device that is to be inserted into the mouth; by coloring the two intraoral and/or extraoral segments different colors, and providing associated written instructions (e.g., green=right, red=left), the mouthpiece provides increased assurance that the mouthpiece will be positioned accurately and not positioned upside down. "Right" and "left" icons can also be provided, as well as "finger icons" showing the positions where the fingers should be placed during placement.

The user can close the lips while the mouthpiece is in position, allowing the user to maintain a typical facial rest position during use.

Importantly, there is no mouthpiece material disposed between the contacting surfaces of the upper and lower teeth. This is advantageous since a significant distance between the upper and lower teeth may reduce the user's ability to swallow with the device in position.

There is no material between the superior surface of the tongue, and the palate. This is also an advantage in terms of swallowing since swallowing requires approximation of the superior tongue surface and the palate to transport ingested material from the mouth to the pharynx.

The mouthpiece can be provided with a flavored element within the intraoral portion, on the surface of the intraoral portion, or on or within the extraoral portion that runs outwardly between the user's upper and lower lips. This flavoring may increase the acceptability of the mouthpiece, as well as promote salivary flow, and swallowing.

The mouthpiece is small and portable. It can be fit into a purse or small carrying bag, or into a typical "sandwich baggie" for easy and clean transport.

The agent(s) delivered to the mouth and oropharynx via the mouthpiece described herein may include, but are not limited to, a fluid, including a gas or liquid. For example, air may be delivered to the posterior oral cavity and oropharynx via the mouthpiece. In this regard, our previous studies, as well as those from other laboratories, have shown that application of air-pulse trains to the oropharynx increases saliva swallowing rates in young and older adults, and activates regions of the human cerebral cortex. Tests were undertaken to determine the effects of oropharyngeal air-pulse: train duration, amplitude, and frequency on saliva swallowing rates in dysphagic stroke and to determine saliva swallowing rates associated with air-pulse application different from swallowing rates associated with a sham condition, in dysphagic stroke.

Figure 8:
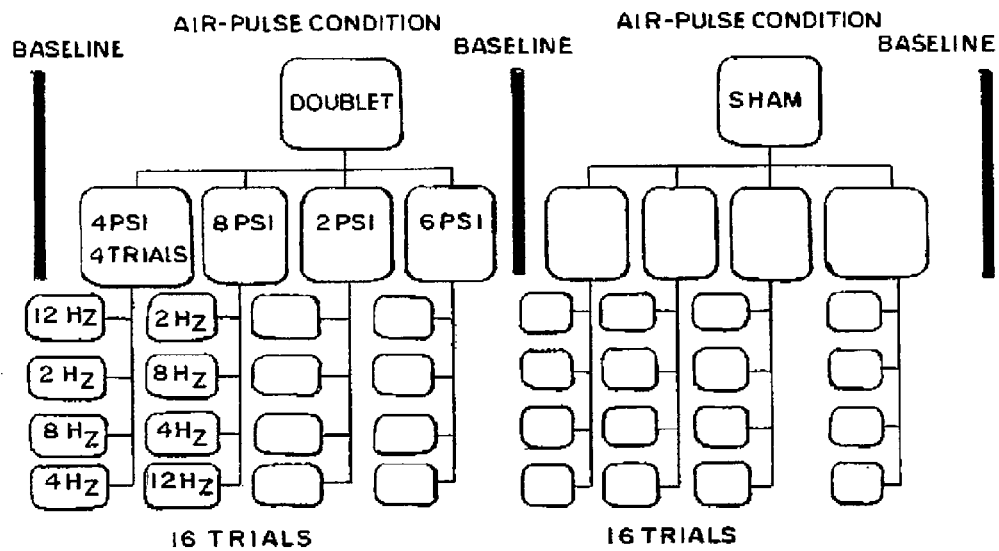
FIG. 8 is a schematic representation of the experimental protocols.

In the first of two experiments, twenty three (23) hospitalized individuals who had dysphagia secondary to a stroke volunteered as subjects. Their median age was 69, and 15 were male. The majority had suffered a stroke involving the right middle cerebral artery territory, however other stroke locations were also represented in the sample. The median days post-stroke at the time of testing was 12 days. Study enrolment was limited to patients who were dependent on tube feeding to some degree; thus, the median FOIS score for the sample was 1.5, with a range of 1 to 3. The experimental protocol is shown in FIG. 8.

Air-pulse trains were delivered bilaterally to the posterior oral cavity and oropharynx via a prototype buccal mouthpiece which was positioned between the subject's upper teeth and the cheek.

Figure 9:
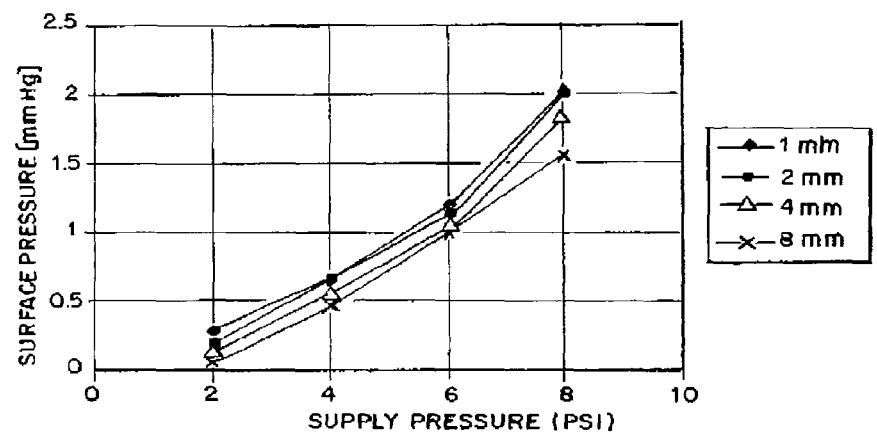
FIG. 9 is a graph showing the supply pressure versus the surface pressure as measured at a plurality of distances form the distal tip of the mouthpiece.

The air-pulse trains were controlled with an Agilent signal generator and LABneb air-pressure regulator, attached to a hospital wall-mounted compressed medical air source. We examined 4 levels of air-pulse train duration: a single pulse, a doublet or two successive pulses, a 2 second train, and a 3 second train; 4 levels of air-pulse amplitude were defined in terms of supply pressures of 2, 4, 6, and 8 psi; and finally, 4 levels of pulse frequency, 2, 4, 8, and 12 Hz, were examined. Based on bench testing, this range of supply pressures corresponded to tip pressures, measured 2 mm to 8 mm from the distal tip of the mouthpiece, of no greater than 2 mm Hg, as shown in FIG. 9.

Figure 10:
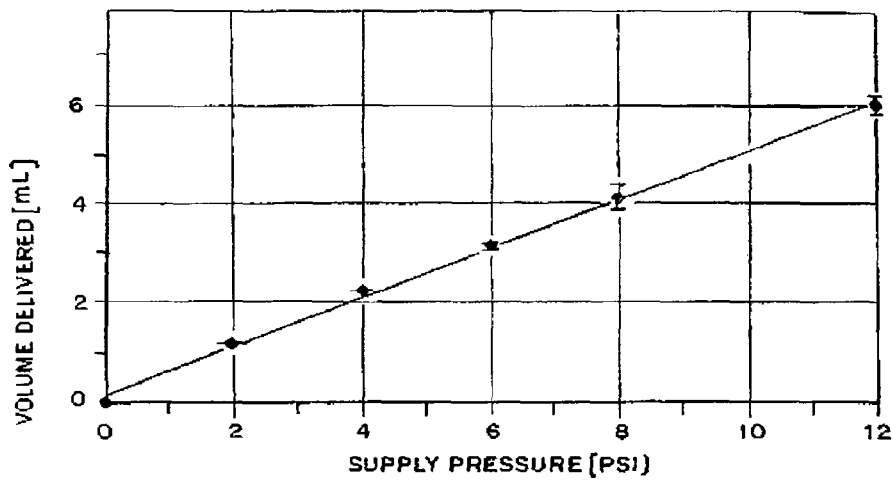
FIG. 10 is a graph showing supply pressure versus volume delivered for 5 ms pulse.

The air volume delivered with a single pulse in this supply pressure range was 1.2 ml to 4.2 ml, as shown by the tables provided below and the graph of FIG. 10.

| SINGLE | Volume Collected [mL] Source Pressure [psi] | | | | | |
|---|---|---|---|---|---|---|
| 50 ms | 0 | 2 | 4 | 6 | 8 | 12 |
| 1 Hz | 0 | 1.2 | 2.3 | 3.1 | 4.2 | 5.8 |
|  | 0 | 1.3 | 2.3 | 3.2 | 4.4 | 6.1 |
|  | 0 | 1.2 | 2.2 | 3.2 | 3.9 | 6 |
| Mean | 0.00 | 1.23 | 2.27 | 3.17 | 4.17 | 5.97 |
| SD | 0.00 | 0.06 | 0.06 | 0.06 | 0.25 | 0.15 |

| | Volume Collected [mL] | | | |
|---|---|---|---|---|
| 2 Sec | 2 PSI | 4 PSI | 6 PSI | 8 PSI |
| 2 Hz | 3.8 | 7.5 | 12.1 | 15.6 |
|  | 4 | 7.4 | 11.8 | 15.8 |
|  | 4.2 | 7.7 | 11.9 | 15.5 |
| Mean | 4.00 | 7.53 | 11.93 | 15.63 |
| SD | 0.20 | 0.15 | 0.15 | 0.15 |
| 4 Hz | 6 | 14.4 | 23.5 | 31.4 |
|  | 6 | 15.1 | 23.7 | 31.6 |
|  | 6.1 | 14.5 | 23.4 | 30.8 |
| Mean | 6.03 | 14.67 | 23.53 | 31.27 |
| SD | 0.06 | 0.38 | 0.15 | 0.42 |
| 6 Hz | 12 | 25.1 | 36.4 | 45 |
|  | 11.8 | 25.2 | 36.3 | 47 |
|  | 11.6 | 24.8 | 36 | 48 |
| Mean | 11.80 | 25.03 | 36.23 | 46.67 |
| SD | 0.20 | 0.21 | 0.21 | 1.53 |
| 8 Hz | 14 | 32.4 | 50 | 62 |
|  | 14.1 | 32.7 | 49 | 62 |
|  | 13.7 | 32.8 | 50 | 62 |
| Mean | 13.93 | 32.63 | 49.67 | 62.00 |
| SD | 0.21 | 0.21 | 0.58 | 0.00 |
| 12 Hz | 20.6 | 44 | 68 | 90 |
|  | 20.4 | 46 | 68 | 89 |
|  | 20.7 | 46 | 68 | 90 |
| Mean | 20.57 | 45.33 | 68.00 | 89.67 |
| SD | 0.15 | 1.15 | 0.00 | 0.58 |

| | Volume Collected [mL] | | | |
|---|---|---|---|---|
| 3 Sec | 2 PSI | 4 PSI | 6 PSI | 8 PSI |
| 2 Hz | 5 | 12 | 22 | 26 |
|  | 4 | 12 | 22 | 28 |
|  | 4 | 12 | 22 | 27 |
| Mean | 4.33 | 12.00 | 22.00 | 27.00 |
| SD | 0.58 | 0.00 | 0.00 | 1.00 |
| 4 Hz | 8 | 28 | 38 | 48 |
|  | 8 | 27 | 38 | 50 |
|  | 8 | 29 | 36 | 50 |
| Mean | 8.00 | 28.00 | 37.33 | 49.33 |
| SD | 0.00 | 1.00 | 1.15 | 1.15 |
| 6 Hz | 14 | 36 | 54 | 70 |
|  | 18 | 38 | 54 | 70 |
|  | 16 | 38 | 55 | 68 |
| Mean | 16.00 | 37.33 | 54.33 | 69.33 |
| SD | 2.00 | 1.15 | 0.58 | 1.15 |
| 8 Hz | 20 | 44 | 70 | 90 |
|  | 22 | 46 | 72 | 92 |
|  | 24 | 46 | 72 | 90 |
| Mean | 22.00 | 45.33 | 71.33 | 90.67 |
| SD | 2.00 | 1.15 | 1.15 | 1.15 |
| 12 Hz | 30 | 62 | 92 | 130 |
|  | 28 | 62 | 92 | 130 |
|  | 29 | 60 | 94 | 130 |
| Mean | 29.00 | 61.33 | 92.67 | 130.00 |
| SD | 1.00 | 1.15 | 1.15 | 0.00 |

Pulse duration was 50 msec throughout.

Air pulse types were presented in blocks of train duration and sham conditions, that is, there were a total of 5 blocks:

single pulse, doublet, 2-sec pulse train, 3-sec pulse train, and sham, two of which are shown here. Successive duration blocks were separated by a 1 min baseline period.

Their order was randomized across subjects. The four air-pulse amplitude conditions were nested as blocks within train duration; and the four levels of air-pulse frequency were further nested within amplitude blocks. There were two orders of each of the amplitude and frequency conditions across subjects. The duration between the onsets of successive pulse trains was approximately 20 sec.

During the sham condition, the air pressure regulator was turned to "0" but the signal generator operated such that the subjects, and experimenters, heard the same noise of the solenoids during the air-pulse and sham conditions.

Dry swallows were identified from the output signals of a Grass throat microphone, a laryngeal movement sensor, and respiratory movement sensor. Two swallows are shown here in relation to three single air-pulse trials. One experimenter observed the subject throughout the session and marked the computer file for swallows and other behaviors. Swallowing rates were computed as number of swallows over duration of the air-pulse condition, from the onset of 1 trial to the onset of the following trial.

Figure 11:
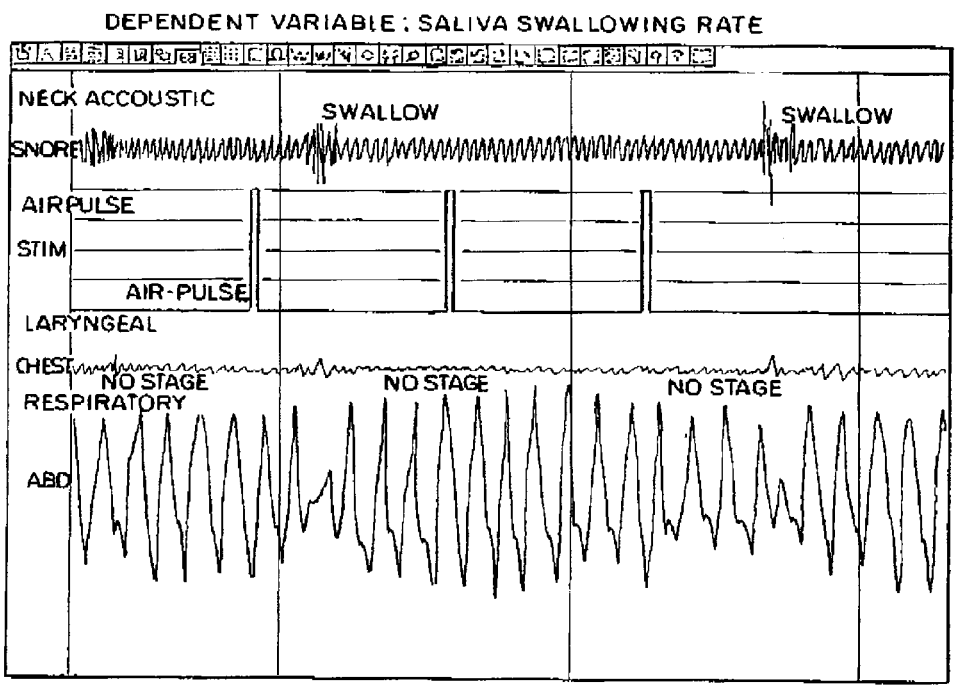
FIG. 11 is a graph showing the saliva swallowing rate.

A repeated measures 1-way ANOVA indicated that there was a main effect of Train Duration on saliva swallowing rate ($p<0.05$). Post-hoc comparisons, with Bonferroni correction, indicated that mean swallowing rates associated with the 2 sec, and the 3 sec train duration conditions were significantly greater than the mean swallowing rate associated with the single pulse condition ($p<0.008$) as shown in FIG. 11.

Figure 12:
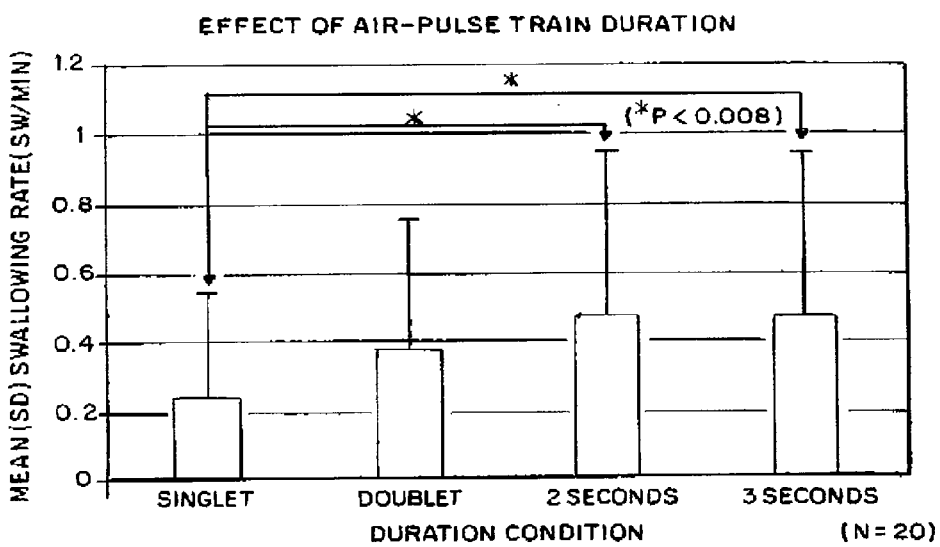
FIG. 12 is a graph showing the effect of air-pulse train duration.
Figure 13:
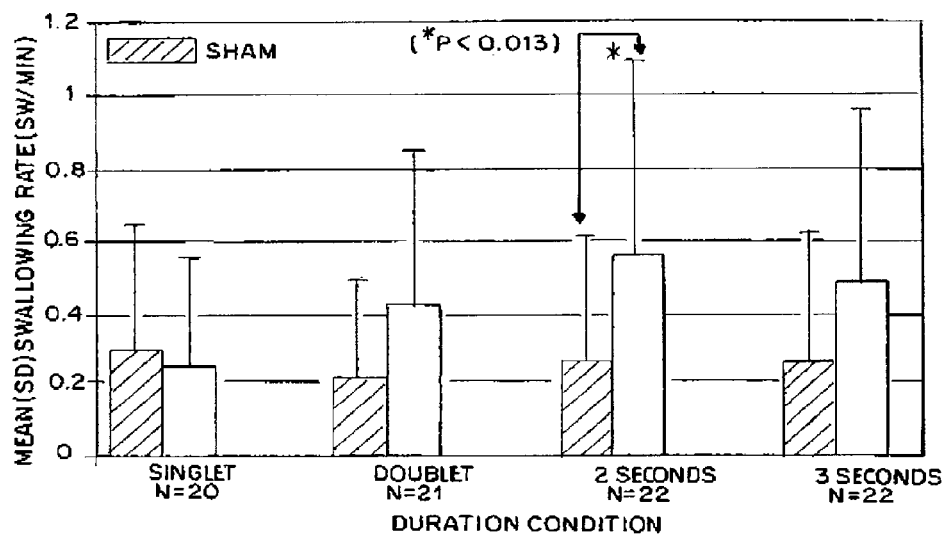
FIG. 13 is a graph showing air-pulse train duration versus sham.

In relation to the sham condition, paired t-tests, again Bonferroni corrected, indicated that the mean swallowing rate associated with the 2 sec train duration condition was significantly greater than the swallowing rate associated with the sham condition ($p<0.013$) as shown in FIGS. 12 and 13.

Figure 14:
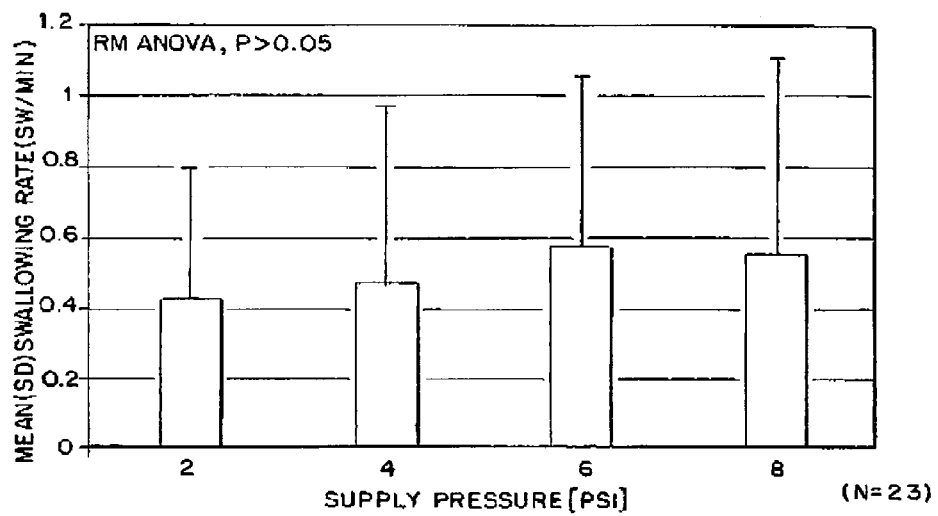
FIG. 14 is a graph showing the effect of air-pulse amplitude.
Figure 15:
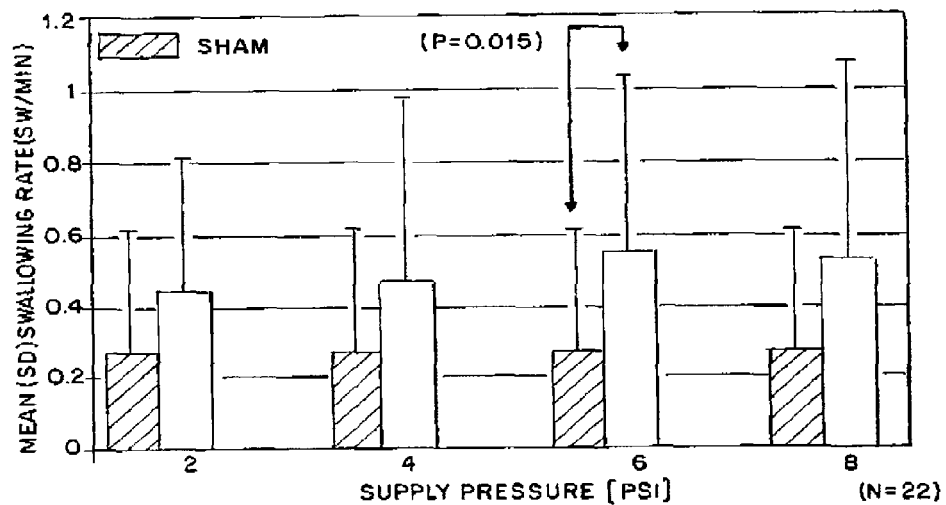
FIG. 15 is a graph showing air-pulse amplitude versus sham.

Turning now to air-pulse amplitude, there was no main effect of air-pulse AMPLITUDE on dry swallowing rate. Compared with the SHAM condition, the 6 psi condition approached the corrected significance level of 0.013 ($p=0.015$). And, the average swallowing rate across the 4 levels of amplitude was significantly greater than the mean swallowing rate associated with the SHAM condition ($p<0.05$) as shown in FIGS. 14 and 15.

Figure 16:
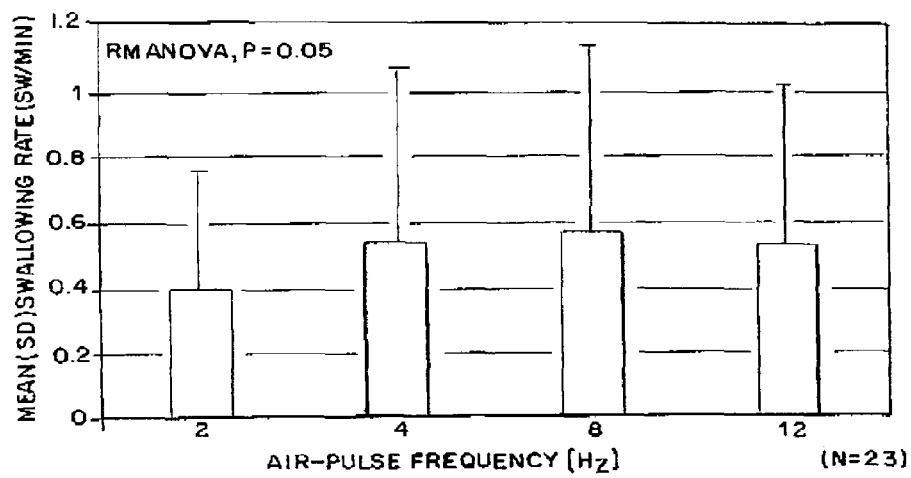
FIG. 16 is a graph showing the effect of air-pulse frequency.
Figure 17:
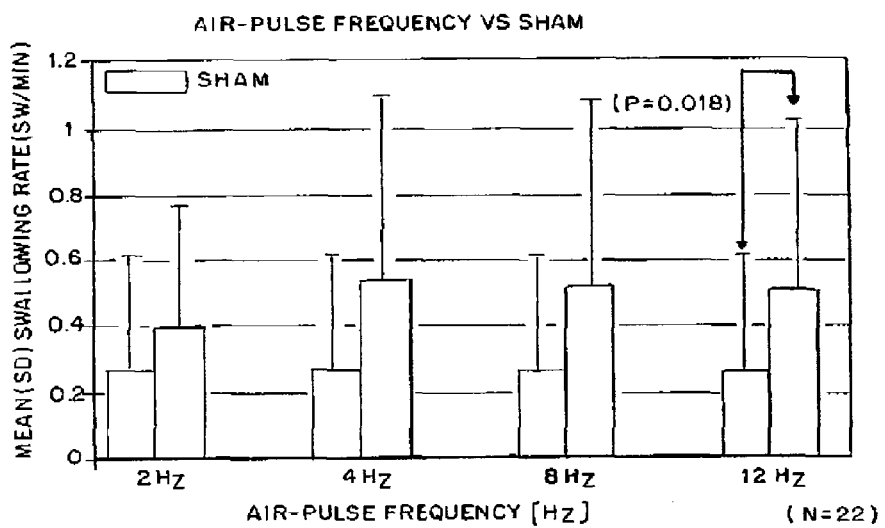
FIG. 17 is a graph showing air-pulse frequency versus sham.

Looking now at air-pulse frequency, there was no mean effect of air-pulse FREQUENCY on dry swallowing rate. Compared with the SHAM condition, the 12 Hz condition approached the corrected significance level ($p=0.018$). The average swallowing rate across the 4 levels of air-pulse frequency was significantly greater than the mean swallowing rate associated with the SHAM condition ($p<0.05$) as shown in FIGS. 16 and 17.

For the air-pulse Duration, Amplitude and Frequency conditions examined, there was considerable variability in dry swallowing rates, as illustrated by the large standard deviations.

In summary, it was determined that swallowing rates showed substantial variability for the air-pulse types examined. Longer air-pulse trains were associated with greater swallowing rates compared with single pulses; swallowing rates associated with 2 sec air-pulse trains were significantly greater than sham. While swallowing rates were not significantly different as a function of air-pulse (i) amplitude, and (ii) frequency conditions, swallowing rates pooled across amplitude or frequency levels were significantly greater than sham. Air-pulse trains, delivered to the posterior mouth and oropharynx via a buccal mouthpiece, were associated with increased saliva swallowing rates in dysphagic stroke.

Dry swallowing rates are influenced by the specific properties of air-pulse trains delivered to the posterior mouth and oropharynx in dysphagia stroke. Air-pulse application is associated with increased dry swallowing rates in dysphagic stroke, supporting the potential of the air-pulse approach in swallowing rehabilitation.

Although there were some significant effects of the air-pulse parameters under study, the effects of air-pulse frequency and amplitude were not marked. With regards to pulse-train duration, the 2-second pulse train appears to be superior to the other pulse types in terms of facilitating swallowing in patients with dysphagia. However, even in the case of duration, there was not a single setting that proved to be categorically superior to the others in terms of associated swallowing rates. This suggests that air pulses that fall within a range of pulse types can be associated with increased swallowing in patients with swallowing impairment. This is an advantage of the air-pulse approach in that the phenomenon does not appear to be limited to a very narrow set of pulse types.

The present finding that air-pulse amplitude and frequency did not have more pronounced effects on swallowing rates suggests the possibility that factors other than air pressure may be important in determining the swallowing response.

Based on this study, air-pulse trains of 2 sec appear to be particularly effective in evoking swallowing in patients with dysphagia following brain injury. Air-pulse trains involving a supply pressure of 6 psi, and involving a frequency of 12 Hz, i.e., involving flow values in the range of 68 mls, also appear to be particularly effective, based on the current testing results in dysphagic patients.

This study demonstrates that oropharyngeal air-pulse trains delivered via a buccal mouthpiece and involving tip pressures (i.e., measured at 2 mm to 8 mm from the tip through bench testing) of less than or equal to 2 mm Hg are effective in increasing saliva swallowing rates in patients with dysphgia following stroke.

The subjects in the current study participated in testing sessions that were approximately 75 minutes in duration. During that period, air-pulse trains were delivered for a period of approximately 20 minutes in 6 minute blocks based on air-pulse train duration, the order of which was randomized across subjects. Subjects were observed to swallow during the various air-pulse duration blocks. There was no trend for swallowing to decrease over the course of the testing session. Based on this experience, an air-pulse application period of approximately 20 minutes is appropriate and preferred in terms of increasing swallowing rates in patients with dysphgia following stroke.

The time between successive air-pulse trains should be (i) short enough that the patient receives an adequate number of bursts per session, but (ii) long enough that the patient does not risk desaturation because of an excessive number of swallowing apneas. Based on the experiment described above, preferred air pulse trains of bursts of 2 sec, 6 psi and 12 Hz, and an inter-stimulus time of 20 sec, the mean+1 sd swallowing rate is less that 3 per min.

Therefore, even patients who respond quite well to the air pulses would not be expected to swallow more than 3 times per minute with an interburst time of 20 sec. A swallowing rate of 3 per min is less than typical swallowing rates for cup drinking, or mealtime eating. Based on this logic, a 20 sec period between the onsets of successive air-pulse trains may be appropriate and thus preferred.

Figure 18:
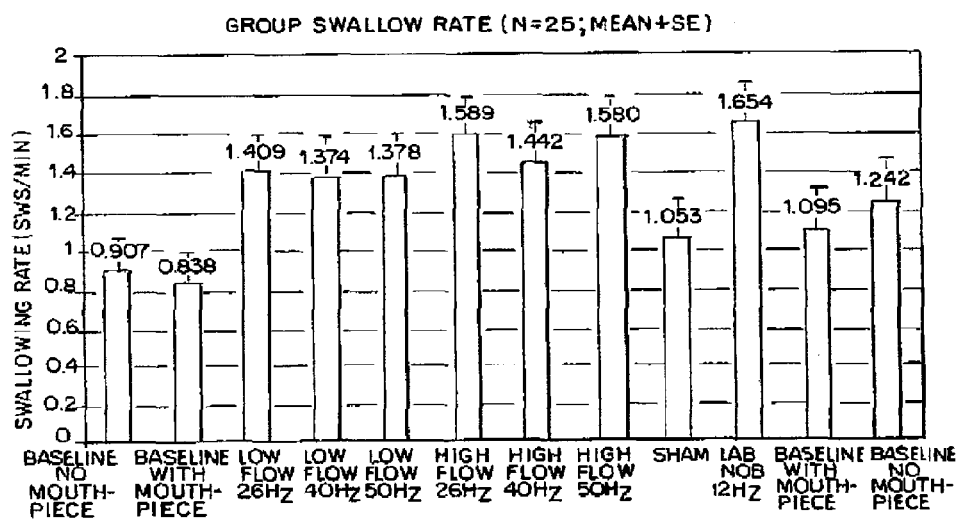
FIG. 18 is a histogram showing the group swallowing rates.
Figure 19:
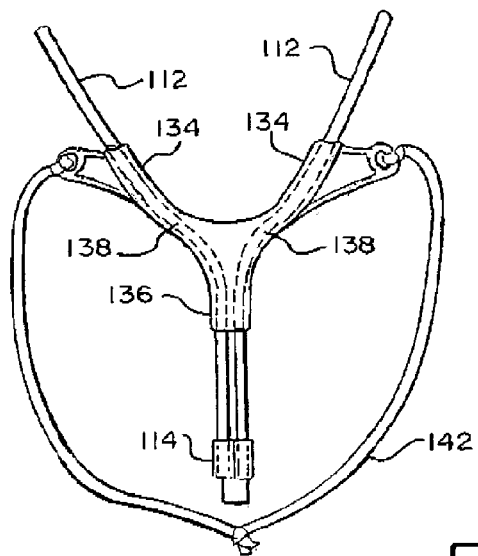
FIG. 19 is a plan view of an alternative embodiment oral device.

Based on our finding that air-pulse trains of 12 Hz are particularly effective, as well as our hypotheses on air flow, a second study was designed to examine higher frequencies, and different air flows, as follows: Oropharyngeal air pulses in the 2 to 12 Hz range are associated with increased swallowing rates in controls and dysphagic patients. However, the effects of higher frequency air pulses, and air flow, are unknown. Therefore, the effects of oropharyngeal air-pulse frequency, and air flow on dry swallowing rates in healthy adults was examined, and compared with a lower frequency air-pulse train employed previously. Methods: Air-pulse trains (duration=3 sec) were delivered to the oropharynx via a prototype buccal over-the-ear mouthpiece in 25 adults (mean±sd age: 26.7±7.9 years; 18 female). Laryngeal, respiratory, and acoustic signals were recorded while six air-pulse conditions were randomly administered to each subject: three Frequency conditions (i.e., 26 Hz, 40 Hz, 59 Hz); crossed with two Flow conditions (i.e., Low Air Flow, High Air Flow) as shown in FIG. 18. A Sham condition, and an 8 Hz air-pulse train previously associated with swallowing, were also examined. Results: While main effects of Frequency, Air Flow, and the Frequency×Air-Flow interaction were not statistically significant (Repeated Measures 2-way ANOVA, perit<0.05), Air Flow approached significance (pobs=0.056). When the data were averaged across Frequency conditions, the mean swallowing rate during the 8 Hz condition was significantly greater than that during the Low Flow condition; however, the 8 Hz and High Flow conditions were not significantly different (paired t-test, perit<0.025). Moreover, swallowing rates during the High Flow and 8 Hz conditions were significantly greater than the Sham swallowing rate, whereas the Low Flow and Sham conditions were not significantly different (paired t-test, perit<0.016). Conclusion: Oropharyngeal air-pulse trains delivered across a range of frequencies, particularly at higher air flows, increase dry swallowing rates in healthy adults, supporting their potential in dysphagia rehabilitation.

In addition to increased dry swallowing during the air-pulse application periods, some subjects were observed to display increased overall arousal, and increased overall motor behaviour, in relation to the air-pulse application. For example, some patients opened their eyes, moved their arms and legs, changed position in their chair, etc, in relation to the air-pulse application. Based on the observation, air-pulse application to the back of the mouth and/or the oropharynx appears to provide a method on increasing overall arousal in individuals with brain damage, and further appears to provide a method of increasing motor behaviour in individuals with brain damage. These methods are particularly important in patients with brain damage, for example, in stroke, where decreased arousal and lack of motor behaviour can be significant challenges during the stroke recovery period that may limit gains in rehabilitation. Thus, the air-pulse approach may be employed in the rehabilitation of patients with brain injury, or possibly dementia, to increase arousal and motor behaviour, in addition to increasing swallowing.

The increased arousal and motor behaviour observed in patients with stroke in association with air-pulse application to the posterior mouth and oropharynx in consistent with our previous finding that oropharyngeal air-pulse application activates the cerebral cortex in healthy control subjects. Various aspects of those findings are further disclosed in U.S. Publication No. 2010/0010400A1, entitled Method of Brain Activation, the entire disclosure of which is hereby incorporated herein by reference. Therefore, for example, cortical activation secondary to air-pulse application may mediate the increases in arousal and motor behaviour observed among stroke patients in the current study.

Generally speaking, the systems described herein are directed to oral mouthpieces. As required, embodiments of the present invention are disclosed herein. However, the disclosed embodiments are merely exemplary, and it should be understood that the invention may be embodied in many various and alternative forms. The Figures are not to scale and some features may be exaggerated or minimized to show details of particular elements while related elements may have been eliminated to prevent obscuring novel aspects. Therefore, specific structural and functional details disclosed herein are not to be interpreted as limiting but merely as a basis for the claims and as a representative basis for teaching one skilled in the art to variously employ the present invention. For purposes of teaching and not limitation, the illustrated embodiments are directed to oral mouthpieces.

As used herein, the terms "comprises" and "comprising" are to construed as being inclusive and open ended rather than exclusive. Specifically, when used in this specification including the claims, the terms "comprises" and "comprising" and variations thereof mean that the specified features, steps or components are included. The terms are not to be interpreted to exclude the presence of other features, steps or components.

What is claimed is:

1. An oral mouthpiece comprising:
a Y-shaped extraoral portion having an inlet portion and a pair of arm portions extending laterally outwardly in opposite directions from said inlet portion, and wherein said arm portions extend rearwardly from said inlet portion in a same rearward direction, wherein said inlet portion defines a single inlet opening, each of said arm portions comprising an attachment portion, wherein each of said attachment portions are positioned on an outboard side of said arm portion and wherein each of said attachment members comprises a wing portion extending laterally outwardly from said arm portion;
a pair of intraoral portions extending from end portions of said arm portions, said intraoral portions each having at least one outlet port adapted to dispense at least one fluid pulse; and
a securing member attached to each of said attachment portions.

2. The oral mouthpiece of claim 1 wherein said securing members each comprise an elastic band formed separately from said extraoral portion.

3. The oral mouthpiece of claim 1 wherein each of said wing portions comprises a concave curved portion adapted to interface with the user.

4. The oral mouthpiece of claim 1 wherein said end portions of said arm portions are spaced rearwardly from said wing portions.

5. The oral mouthpiece of claim 1 where each of said intraoral portions includes a plurality of exit ports.

6. The oral mouthpiece of claim 1 wherein said intraoral portions have a smaller outside diameter than said extraoral portions.

7. The oral mouthpiece of claim 1 wherein said extraoral and said intraoral portions are integrally formed.

8. The oral mouthpiece of claim 1 wherein said attachment portions each comprise a looped region.

9. The oral mouthpiece of claim 1 wherein said securing members each comprise a loop.

10. The oral mouthpiece of claim 1 further comprising a single input tube interfitted with said single inlet opening.

11. The oral mouthpiece of claim 10 further comprising a control unit connected to said single input tube.

12. The oral mouthpiece of claim 11 wherein said control unit comprises a pressurized air source.

* * * * *